US012668837B2

(12) United States Patent
Manaresi et al.

(10) Patent No.: US 12,668,837 B2
(45) Date of Patent: Jun. 30, 2026

(54) METHOD FOR ANALYSING LOSS-OF-HETEROZYGOSITY (LoH) FOLLOWING DETERMINISTIC RESTRICTION-SITE WHOLE GENOME AMPLIFICATION (DRS-WGA)

(71) Applicant: Menarini Silicon Biosystems S.p.A., Castel Maggiore (IT)

(72) Inventors: Nicolò Manaresi, Castel Maggiore (IT); Marianna Garonzi, Castel Maggiore (IT); Alberto Ferrarini, Castel Maggiore (IT); Claudio Forcato, Castel Maggiore (IT)

(73) Assignee: Menarini Silicon Biosystems S.p.A., Castel Maggiore (IT)

( * ) Notice: Subject to any disclaimer, the term of this patent is extended or adjusted under 35 U.S.C. 154(b) by 1169 days.

(21) Appl. No.: 17/631,269

(22) PCT Filed: Jul. 29, 2020

(86) PCT No.: PCT/IB2020/057149
§ 371 (c)(1),
(2) Date: Jan. 28, 2022

(87) PCT Pub. No.: WO2021/019459
PCT Pub. Date: Feb. 4, 2021

(65) Prior Publication Data
US 2023/0175053 A1 Jun. 8, 2023

(30) Foreign Application Priority Data
Jul. 30, 2019 (IT) ............................ 1029000013335

(51) Int. Cl.
*C12Q 1/6869* (2018.01)
*G16B 20/10* (2019.01)
*G16B 30/10* (2019.01)

(52) U.S. Cl.
CPC ........... *C12Q 1/6869* (2013.01); *G16B 20/10* (2019.02); *G16B 30/10* (2019.02)

(58) Field of Classification Search
None
See application file for complete search history.

(56) References Cited

U.S. PATENT DOCUMENTS

| | | | |
|---|---|---|---|
| 7,424,368 B2 | 9/2008 | Huang et al. | |
| 2021/0098079 A1 | 4/2021 | Choy et al. | |
| 2022/0028481 A1 | 1/2022 | Pozzorini et al. | |

FOREIGN PATENT DOCUMENTS

| | | |
|---|---|---|
| CN | 112885406 A | 6/2021 |
| CN | 114269948 A | 4/2022 |

(Continued)

OTHER PUBLICATIONS

Czyz, Z.T. and Klein, C.A., 2015. Deterministic whole-genome amplification of single cells. In Whole Genome Amplification: Methods and Protocols (pp. 69-86). New York, NY: Springer New York. (Year: 2015).*

(Continued)

*Primary Examiner* — G. Steven Vanni
*Assistant Examiner* — Meredith Abbott Vassell
(74) *Attorney, Agent, or Firm* — MARSHALL, GERSTEIN BORUN LLP

(57) ABSTRACT

A method for analyzing loss-of-heterozygosity (LoH) in at least one sample comprising genomic DNA can include: a. providing the sample comprising genomic DNA; b. carrying out a deterministic restriction-site whole genome amplification (DRS-WGA) of said genomic DNA; c. preparing a massively parallel sequencing library from the product of said DRS-WGA; d. carrying out low-pass whole genome sequencing at a mean coverage depth of <1 on said massively parallel sequencing library; e. aligning the reads obtained in step d. on a reference genome for said at least (Continued)

one sample; f. extracting the allelic content at a plurality of loci, wherein said plurality of loci comprises polymorphic loci and/or heterozygous loci; g. assigning an LoH score to at least one genomic window of said reference genome for said at least one sample as a function of the number of loci with at least two different alleles in said plurality of loci.

28 Claims, 20 Drawing Sheets

(56)                    References Cited

FOREIGN PATENT DOCUMENTS

| EP | 2794907 A1 | 10/2014 |
|----|-----------|---------|
| WO | WO-2000/017390 A1 | 3/2000 |
| WO | WO-2017/178655 A1 | 10/2017 |
| WO | WO-2019/016401 A1 | 1/2019 |
| WO | WO-2020/208181 A1 | 10/2020 |
| WO | WO-2021/037016 A1 | 3/2021 |

OTHER PUBLICATIONS

Shendure, J., Balasubramanian, S., Church, G.M., Gilbert, W., Rogers, J., Schloss, J.A. and Waterston, R.H., 2017. DNA sequencing at 40: past, present and future. Nature, 550(7676), pp. 345-353. (Year: 2017).*

Bolognesi, C., et al., 2016. Digital sorting of pure cell populations enables unambiguous genetic analysis of heterogeneous formalin-fixed paraffin-embedded tumors by next generation sequencing. Scientific reports, 6(1): 20944, pp. 1-14. (Year: 2016).*

Viswanathan, S.R., Ha, G., Hoff, A.M., Wala, J.A., Carrot-Zhang, J., Whelan, C.W., Haradhvala, N.J., Freeman, S.S., Reed, S.C., Rhoades, J. and Polak, P., 2018. Structural alterations driving castration-resistant prostate cancer revealed by linked-read genome sequencing. Cell, 174(2), pp. 433-447. (Year: 2018).*

Andriani, G.A., et al., 2019. A direct comparison of interphase FISH versus low-coverage single cell sequencing to detect aneuploidy reveals respective strengths and weaknesses. Scientific reports, 9(1):10508, pp. 1-7. (Year: 2019).*

International Search Report and Written Opinion for Corresponding International Application No. PCT/IB2020/057149, mailing date Oct. 7, 2020.

Allard WJ. et al., Tumor Cells Circulate in the Peripheral Blood of all Major Carcinomas but no in Healthy Subjects or Patients with Nonmalignant Diseases, Clinical Cancer Research, vol. 10, pp. 6897-6904, Oct. 15, 2004.

Arneson et al., Comparison of Whole Genome Amplification Methods for Analysis of DNA Extracted from Microdissected Early Breast Lesions in Formalin-Fixed Paraffin-Embedded Tissue, Research Article, ISRN Oncology, vol. 2012, Article ID 710692, pp. 1-10, 2012.

Benjamini et al., Controlling the False Discovery Rate: a Practical and Powerful Approach to Multiple Testing, J. R. Statist. Soc. B, (1995) vol. 57, No. 1, pp. 289-300.

Binder et al, A New Workflow for Whole-Genome Sequencing of Single Human Cells, Human Mutation, vol. 35, No. 10, Aug. 18, 2014, pp. 1260-1270.

Boeva et al., Genome Analysis, Control-fee calling of copy number alterations in deep-sequencing data using GC-content normalization, Bioinformatics, vol. 27 No. 2. pp. 268-269, 2011.

Boeva et al., Genome Analysis, Control-FREEC: a tool for assessing copy number and allelic content using next-generation sequencing data, Bioinformatics, vol. 28 No. 3. pp. 423-425, 2012.

Borgstrom et al., Comparison of whole genome amplification techniques for human single cell exome sequencing, PLOS one, 12(2) Feb. 16, 2017.

Czyz et al., Reliable Single Cell Array CGH for Clinical Sample, PLOS ONE, vol. 9, Issue 1, e85907, Jan. 2014.

Ferrarini et al., A streamlined workflow for single-cells genome-wide copy-number profiling by low-pass sequencing of LM-PCR whole-genome amplification products, PLOS ONE, vol. 13, No. 3, Mar. 1, 2018, pp. 0193689.

Forcato et al, Multi-level genomic profiling of heterogeneous FFPE tumors with low tumor cellularity sorted by DEPArray technology, 50th European Society of Human Genetics Conference, ESHG 2017,vol. 26, Oct. 1, 2018, pp. 593-594.

Green et al, A new method to detect loss of heterozygosity using cohort heterozygosity comparisons, BMC Cancer, Biomed Central, London, GB, vol. 10, No. 1, May 12, 2010, p. 195.

Ha et al.., Integrative analysis of genome-wide loss of heterozygosity and mono-allelic expression at nucleotide resolution reveals disrupted pathways in triple negative breast cancer, May 21, 2012 (May 21, 2012), p. 1-38.

Harchaoui et al., Catching change-points with Lasso, Advances in Neural Information Processing Systems 20, 2008, pp. 617-624.

Hodgkinson et al., Tumorigenicity and genetic profiling or circulating, Natural Medicine, vol. 20, No. 8, Aug. 2014, pp. 897-903.

Mohlendick et al., A Robust Method to Analyze Copy Number Alterations of Less than 100 kb in Single Cells Using Oligonucleotide Array CGH, PLUS ONE, vol. 8, Issue 6, e67031, pp. 1-11, Jun. 2013.

Normand et al., Comparison of three whole genome amplification methods for detection of genomic aberrations in single cells, Prenatal Diagnosis, vol. 36, pp. 823-830, 2016.

Seshan et al., Package 'DNAcopy' DNA copy number data analysis, Version 1.58.0, Oct. 15, 2019.

Stoecklein et al., SCOMP Is Superior to Degenerated Oligonucleotide Primed-Polymerase Chain Reaction for Global Amplification of Minute Amounts of DNA from Microdissected Archival Tissue Samples, American Journal of Pathology, vol. 161 No. 1, Jul. 2002, pp. 43-51.

Wang et al, Identifying Human Genome-Wide CNV, LOH and UPD by Targeted Sequencing of Selected Regions, PLOS ONE, vol. 10, No. 4, Apr. 28, 2015, pp. e0123081.

Watkins et al., Genomic scars as biomarkers of homologous recombination deficiency and drug response in breast and ovarian cancers, Breast Cancer Research, 2014, 16:211, pp. 1-11.

Zahn et al., Scalable whole-genome single-cell library preparation without preamplification, Nature Methods, DOI:10.1038/NMETH. 4140, Jan. 9, 2017, pp. 1-10.

Chinese Patent Application No. 202080068436.8, Office Action, dated Jun. 24, 2024.

Xu et al., Single Cell Whole Genome Amplification Technology and Application, Prog. Biochem. Biophys., 46(4):342-352 (2019).

* cited by examiner

B)

A)

D)

C)

METHOD FOR ANALYSING LOSS-OF-HETEROZYGOSITY (LoH) FOLLOWING DETERMINISTIC RESTRICTION-SITE WHOLE GENOME AMPLIFICATION (DRS-WGA)

CROSS-REFERENCE TO RELATED APPLICATIONS

This patent application is a U.S. national phase of International Patent Application No. PCT/IB2020/057149 filed Jul. 29, 2020, which claims the benefit of priority from Italian patent application no. 102019000013335 filed on Jul. 30, 2019, the repsective dislosures of which are each incorporated herein by reference in their entireties.

TECHNICAL FIELD OF THE INVENTION

The present invention relates to a method for analysing loss-of-heterozygosity (LoH) in a sample from low-pass whole genome sequencing data from deterministic restriction-site whole genome amplification (DRS-WGA), achieving single-cell resolution, with or without the use of normal controls. The method can be applied in several single-cell applications, such as in oncology, including analysis of circulating tumor cells, and single-cell heterogeneity in tissue samples, or reproductive medicine, including pre-implantation genetic screening (PGS).

PRIOR ART

Whole Genome Amplification (WGA) of single cell genomic DNA is often required for obtaining more DNA in order to simplify and/or allow different types of genetic analyses, including sequencing, SNP detection etc. WGA with a LM-PCR based on a Deterministic Restriction Site (in the following DRS-WGA) is known from WO2000/017390.

Importantly, DRS-WGA has been shown to be the best-in-class WGA method in many perspectives, in particular in terms of lower allelic drop-out from single cells (Borgstrom et al., 2017; Normand et al., 2016; Babayan et al., 2016; Binder et al., 2014).

A LM-PCR based, DRS-WGA commercial kit (Amplil™ WGA kit, Silicon Biosystems) has been used in Hodgkinson C. L. et al., Nature Medicine 20, 897-903 (2014). In this work, a Copy-Number Analysis by low-pass whole genome sequencing on single-cell WGA material was performed, carrying out digestion of the WGA adaptors and fragmentation prior to Illumina barcoded adaptor ligation for sequencing.

WO2017/178655 and WO2019/016401A1 teach a simplified method to prepare massively parallel sequencing libraries from DRS-WGA (e.g. Amplil) or MALBAC for low-pass whole genome sequencing and copy number profiling. In Ferrarini et al., "A streamlined workflow for single-cells genome-wide copy-number profiling by low-pass sequencing of LM-PCT whole-genome amplification products," PLoSONE 13(3):e0193689 (2018), the method performance of WO2017/178655 using the Ion Torrent Platform has been detailed with reference to copy number profiling.

Amplil™ WGA is compatible with array Comparative Genomic Hybridization (aCGH). Indeed several groups (Moehlendick B, et al., 2013, PLoS ONE 8(6): e67031; Czyz Z T, et al., 2014, PLoS ONE 9(1): e85907) showed that it is suitable for high-resolution copy number analysis. However, the aCGH technique is expensive and labor intensive, so that different methods such as low-pass whole-genome sequencing (LPWGS) for detection of somatic Copy-number alterations (CNA) may be desirable.

DRS-WGA has been shown to be better than DOP-PCR for the analysis of copy-number profiles from minute amounts of microdissected FFPE material (Stoecklein et al., Am J Pathol. 2002 July; 161(1):43-51; Arneson et al., ISRN Oncol. 2012; 2012:710692. doi: 10.5402/2012/710692. Epub 2012 Mar. 14.), when using array CGH, metaphase CGH, as well as for other genetic analysis assay such as Loss of heterozygosity using targeted primers and PCR for analysis of selected microsatellites.

U.S. Pat. No. 7,424,368 B2 teaches a method for estimating the copy number of a genomic region in an experimental sample, comprising the analysis of SNPs using microarray. Microarray techniques are less processive and flexible with respect to next-generation sequencing, and do not provide absolute counts but only relative signals. Besides, there are set-up costs related to the synthesis of the probes and the manufacturing of a microarray, contrary to next generation sequencing (NGS).

Zahn H. et al., Nature Methods, volume 14, pages 167-173 (2017), teaches a method to prepare massively parallel single-cell libraries without pre-amplification, and shows simultaneous inference of CNAs and LoH on the bulk-equivalent of SA501X3F cell line. This approach, however, requires a relatively large number of single-cells (48). In addition, heterozygous SNP positions must be determined in order to carry out the analysis using TITAN (Ha G. et al., 2014, Genome Research 24(11)).

This method has the following drawbacks.

1. It is not compatible with the use of whole-genome amplified libraries, but WGA is indeed desirable in many cases, for example when dealing with CTCs, as re-analysis of a different aliquot of the WGA product may be required for gaining additional information, e.g. on SNVs in onco-genes or tumor suppressor genes, at the single cell level from each individual cell, for different purposes including for biomarker discovery or for assessing other known biomarkers of efficacy which may not be inferred just by low-pass WGS.

2. In certain applications, such as pre-implantation genetic screening (PGS) or pre-implantation genetic diagnosis (PGD), a single cell may only be available, so that the Zahn et al. approach is clearly not applicable.

3. In certain applications, multiple cells may be available for analysis, but they may still be insufficient to provide enough information to use the approach of Zahn et al. For example, the number of CTCs collected from a 7.5 ml blood draw from metastatic patients using CELLSEARCH system is in the majority of cases below 10 (Allard W J. et al., 2004, Clin Cancer Res., October 15; 10(20):6897-904, see Table 2).

In oncology, genome wide evaluation of LoH has been shown to be important in several contexts, including the assessment of the so-called BRCAness signature, associated with efficacy of platinum therapy and poly(ADP-ribose) polymerase (PARP)—inhibitors in several cancer types (e.g. Watkins et al., Breast Cancer Research 2014, 16:211). In addition, analysis of LoH at the BRCA1 and BRCA2 loci in the tumor of germline-mutated individuals has been shown to be important for therapy efficacy.

In pre-implantation genetic screening (PGS) or pre-implantation genetic diagnosis (PGD), it is desirable to assess Uniparental disomy (UPD), occurring when a person receives two copies of a chromosome, or of part of a chromosome, from one parent and no copy from the other parent. However, this kind of information is not available from standard LPWGS workflows when using conventional bioinformatic pipelines and analysis methods.

There is a need to provide a method that allows to infer genome-wide LoH status (and/or gene specific LoH status) down to single-cell resolution, overcoming one or more of the following limitations inherent in the state of the art:

need of high coverage whole-genome sequencing, or equivalently, large number of single-cell low-pass sequencing producing a bulk-equivalent with high coverage;

mandatory requirement for a normal control;

impossibility to reliably reanalyse a single cell for verification or additional targeted genomic information.

For CTC analysis, as well as for other single-cell analysis applications, such as prenatal diagnosis on blastocysts and circulating fetal cells harvested from maternal blood, it would be desirable to have an efficient method, combining the reproducibility and quality of DRS-WGA with the capability to analyse genome-wide LoH along with copy-number variants (CNVs), from the same low-pass sequencing data.

In addition, it would be desirable to determine whole-genome copy number profile and LoH also from minute amounts of cells, FFPE or tissue biopsies.

Binder V. et al., "A new workflow for whole-genome sequencing of single human cells", Human mutation, Vol. 35, No. 10, pp. 1260-1270, 2014, discloses a workflow combining an efficient adapter-linker PCR-based WGA method with second-generation sequencing. This approach allows comparison of single cells at base pair resolution. This method however is based on genotyped SNPs, i.e. polymorphic genomic positions for which a sufficient coverage can be obtained so as to call a genotype with a certain confidence.

The above said method and the method of the present invention have significantly different aims. The aim of the present invention is not to genotype polymorphic positions as in Binder et al., but instead to infer genome-wide LoH status (and/or gene specific LoH status) down to single-cell resolution.

The method of Binder et al. implies a number of reads greater by two orders of magnitude. Instead, according to the present invention LoH can be called from a single sample e.g. starting from 2 million reads, which corresponds to less than 1% of the reads used in Binder et al.

SUMMARY OF THE INVENTION

It is therefore an object of the present invention to provide a method for analysing LoH which overcomes the drawbacks of prior art methods.

In particular, the object of the present invention is to provide a method for analysing LoH from few cells, down to single-cell resolution, following whole genome amplification, that involves the use of less cells for analysis, less normal controls, less sequencing reads per cell than generally reported in the art.

This object is achieved by the method as defined in claim 1.

DEFINITIONS

Figure 1:
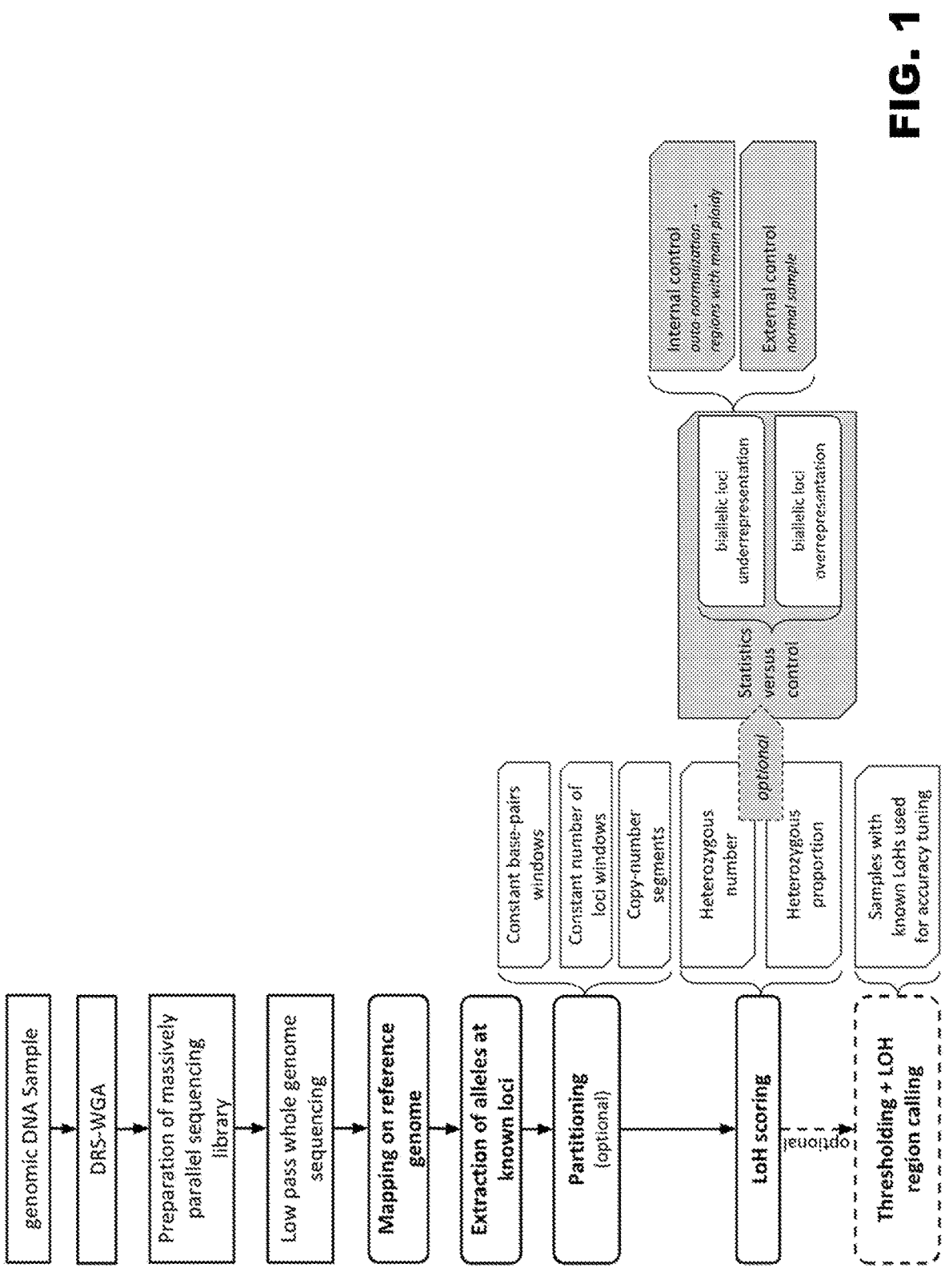
FIG. 1 shows a block diagram summarizing the steps of the method according to the invention.

Unless defined otherwise, all technical and scientific terms used herein have the same meaning as commonly understood by one of ordinary skill in the art to which this invention pertains. Although many methods and materials similar or equivalent to those described herein may be used in the practice or testing of the present invention, preferred methods and materials are described below. Unless mentioned otherwise, the techniques described herein for use with the invention are standard methodologies well known to persons of ordinary skill in the art.

By the expression "massive-parallel next generation sequencing (NGS or MPS)" there is intended a method of sequencing DNA comprising the creation of a library of DNA molecules separated spatially and/or in time, clonally sequenced (with or without prior clonal amplification).

Examples include the Illumina platform (Illumina Inc), the Ion Torrent platform (Thermo Fisher Scientific Inc), the Pacific Biosciences platform, the MinIon (Oxford Nanopore Technologies Ltd).

By the expression "low-pass whole genome sequencing" there is intended a whole genome sequencing at mean sequencing depth lower than 3 with reference to the entire Reference Genome.

By the expression "mean sequencing depth" there is intended here, on a per-sample basis, the total number of bases sequenced, mapped to the reference genome, divided by the total reference genome size. The total number of bases sequenced and mapped can be approximated to the number of mapped reads time the average read length.

By the expression "reference genome" there is intended a reference DNA sequence for the specific species.

By the term "locus" (plural "loci") there is intended a fixed position on a chromosome (relative to the reference genome).

By the expression "polymorphic locus" there is intended a locus having 2 or more alleles with an observed frequency larger than 1% in a population.

By the expression "heterozygous locus" there is intended a locus having 2 or more alleles observed in a specific sample.

By the expression "genomic window" there is intended an interval of the reference genome included in a single chromosome, having fixed or variable length.

By the expression "genomic region" there is intended an interval comprising one or more adjacent genomic windows in the same chromosome.

By the expression "covered genome" there is intended the portion of reference genome covered by at least one read.

By the term "read" there is intended the piece of DNA that is sequenced ("read") by the sequencer.

By the expression "copy-number region" there is intended a genomic region associated to the same copy number value.

By the expression "segmented copy-number region" there is intended a genomic region associated to the same copy number value as a result of a bioinformatic analysis of CNAs.

By the expression "tumor suppressor gene" there is intended a gene for which loss-of-function, due for example to sequence variants—germline or somatic-, is associated with increased probability of occurrence of a tumor.

By the expression "reduction ratio" there is intended the total number of bases of fragments, obtained by in-silico digestion of a reference genome according to a restriction enzyme employed in a DRS-WGA, comprised in a specified base-pair range, divided by the total number of bases in the reference genome.

By the expression "loss-of-heterozygosity" or "LoH" there is intended the loss of one of the alleles in a genomic region.

By the expression "LoH call" there is intended the assignment of the presence of LoH (in a genomic region).

By the expression "allelic content" there is intended the composition in terms of alleles detected at a locus.

For simplicity, in the description of the invention a locus will be referred to as homozygous or monoallelic interchangeably, if only one allele is detected, and heterozygous or biallelic, in case of presence of at least two alleles, regardless of the real genotype of the locus, unless otherwise noted.

DETAILED DESCRIPTION OF THE INVENTION

With reference to FIG. 1, the method according to the present invention for analysing loss-of-heterozygosity (LoH) in at least one sample comprising genomic DNA comprises the following steps.

In step a, at least one sample comprising genomic DNA is provided.

In step b, a deterministic restriction-site whole genome amplification (DRS-WGA) of said genomic DNA is carried out.

In step c, a massively parallel sequencing library is prepared from the product of said DRS-WGA.

In step d, low-pass whole genome sequencing is carried out at a mean coverage depth of <1, preferably <0.05, more preferably <0.01 on said massively parallel sequencing library.

In step e, the reads obtained in step d. are aligned on a reference genome for said at least one sample.

In step f, the allelic content at a plurality of loci is extracted. Said plurality of loci comprises polymorphic loci and/or heterozygous loci.

In step g, an LoH score is assigned to at least one genomic window of said reference genome for said at least one sample as a function of the number of loci with at least two different alleles in said plurality of loci.

Preferably, a step of size selection is performed before, during or after step c. of preparing a massively parallel sequencing library and the step of preparing a massively parallel sequencing library does not include a random fragmentation step.

The step of size-selection preferably retains fragments in the range from 100 to 800 base pairs.

In certain embodiments of the invention, size-selection preferably retains fragments in the range from 300 to 450 base pairs.

In certain embodiments of the invention, the peak of fragments retained in the step of size-selection is preferably centered on a base pair range from 150 bp to 600 bp, more preferably, the step of size selection retains fragments in the range 425-575 base pairs.

Preferably, the at least one genomic window:

has a constant width in base pairs, or has a constant number of said plurality of loci, or is selected from the group consisting of a chromosome, a chromosome arm, and a segmented copy-number region.

The plurality of loci preferably comprises polymorphic loci obtained from a database, such as dbSNP, for the reference genome of said at least one sample, or obtained by genotyping a reference set of samples.

As an alternative, the plurality of loci preferably comprises known heterozygous loci for the control-sample.

When the genomic window has a constant width in base pairs, or has a constant number of the plurality of loci, or the plurality of loci comprises polymorphic loci for the reference genome of said sample, the LoH score preferably corresponds to the number of heterozygous loci in said at least one genomic window.

Preferably, the LoH score corresponds to the proportion of heterozygous loci with respect to the total number of polymorphic loci in the at least one genomic window.

The LoH score preferably corresponds to the p-value of a statistical test.

The statistical test preferably assesses the significance of over-representation of biallelic loci with respect to sequencing and WGA error rates or the significance of under-representation of biallelic loci with respect to a control sample.

The control sample preferably comprises at least one genomic region at main ploidy from the at least one sample.

The control sample is preferably an at least one normal sample, which is more preferably obtained from the same individual under test from which said at least one sample was obtained. In the case of oncology, the control sample is preferably a normal (non-tumor) sample.

In the case of circulating fetal cells, the control sample is preferably a maternal sample. Alternatively when a paternal sample is available, it may be a paternal sample or a combination of the maternal and paternal sample.

Availability of maternal and/or paternal genotype can be exploited to select a subset of loci which are known to be heterozygous in said parental control.

Preferably, if said LoH score passes a threshold for a genomic window, said genomic window is called as being in LoH. In this case, the method more preferably comprises a step of assigning an LoH status to at least one genomic region if the LoH scores for each genomic window comprised in that region passes said threshold or a step of assigning an LoH status to at least one genomic region as a function of the LoH status of genomic windows comprised in that region.

More preferably, the at least one genomic region comprises a tumor suppressor gene, which is selected even more preferably from the group consisting of BRCA1, BRCA2, PALB2, TP53, CDKN2A, RB1, APC, PTEN, CDKN1B, DMP1, NF1, AML1, EGR1, TGFBR1, TGFBR2 and SMAD4.

The at least one sample preferably has a purity of at least 50%. More preferably said at least one sample is a single cell.

Locus to fragment-length univocal relationship in DRS-WGA More in detail, the method according to the invention exploits the fact that in DRS-WGA, such as the Amplil™ WGA, each locus in the genome is represented in the WGA library only in fragments having a specific length in base-pairs. This property may be designated "Locus to Fragment-Length Univocal Relationship" (L2FLUR). Considering a general normal locus, e.g. a locus for a polymorphic SNP, said locus will be represented only in a fragment of a given length, equal to the size of the corresponding fragment (measured on either of the single-strands) following digestion by the restriction enzyme, plus double the length of the universal WGA adaptors (the length of the LIB1 primer in case of Amplil WGA). When the WGA is sequenced following library preparation according to Amplil LowPass kits, a predictable additional length is introduced linked to the sequencing adaptors and barcodes lengths, which are known.

Non-idealities such as undigested restriction sites or sequence variants, as well as other factors, may impact and skew the frequency of representation of a given fragment in the WGA product with respect to what would be expected theoretically. These factors are typically moderate, and in addition, insofar that they are reproducible, their non-random nature can be partially offset by compensating their effect. Therefore, their effect will be neglected in the present description, unless otherwise noted.

Reduced Representation of the Genome

In the method according to the invention, the L2FLURL property is exploited to produce a reduced representation of the genome, whereby the low-pass sequencing data, for a given number of reads, achieves an effective higher coverage of the covered genome, by effectively reducing the size of the covered genome with respect to the original size of the sample reference genome. In other words, size selection of the WGA fragments produces a deterministic subsampling of the reference genome. The term "deterministic" is essential, in that—increasing the number of reads—the same genomic loci are eventually resampled (see FIG. 2).

Figure 2:
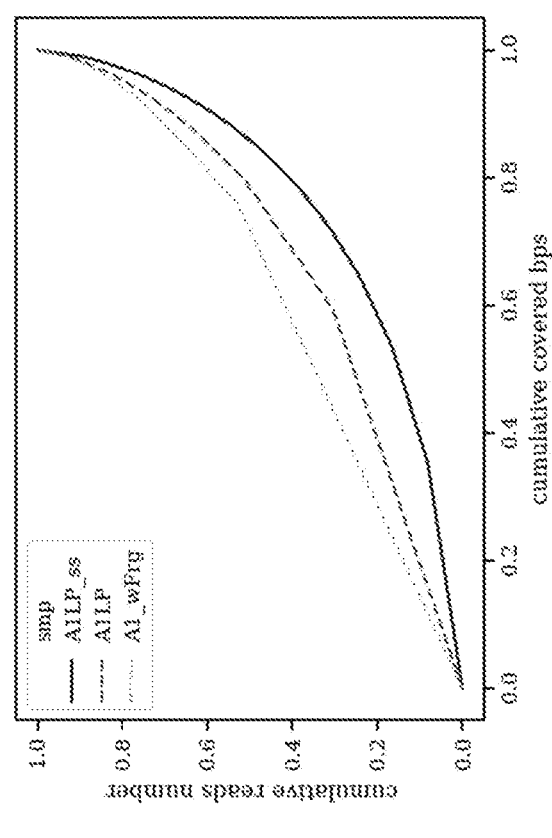
FIG. 2 shows the effect of reduced genome representation on the observed coverage.
Figure 2:
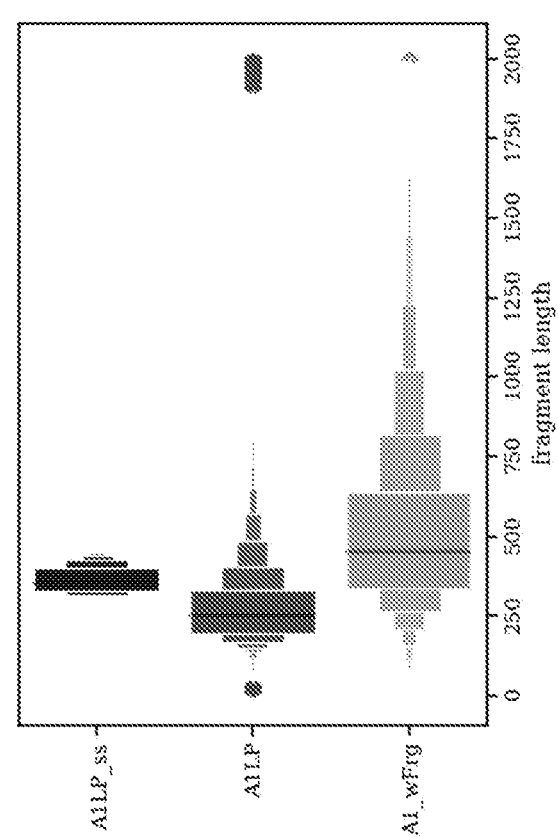
Figure 2:
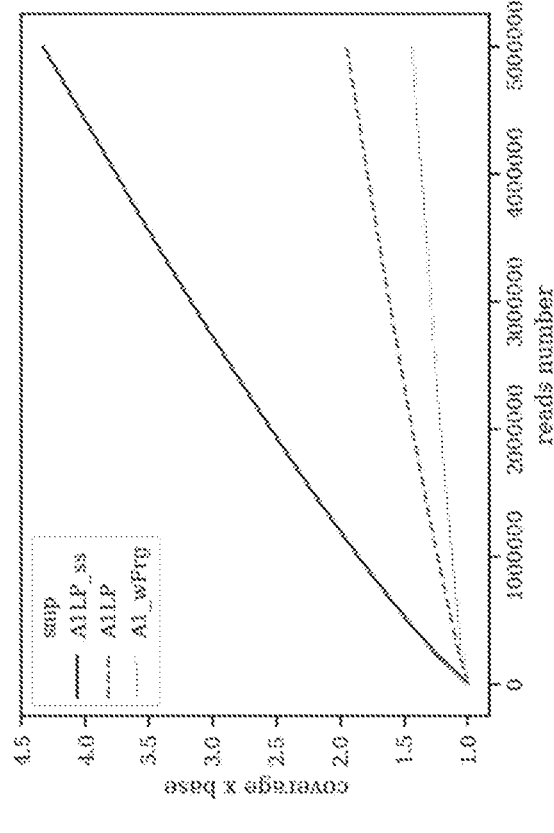
Figure 2:
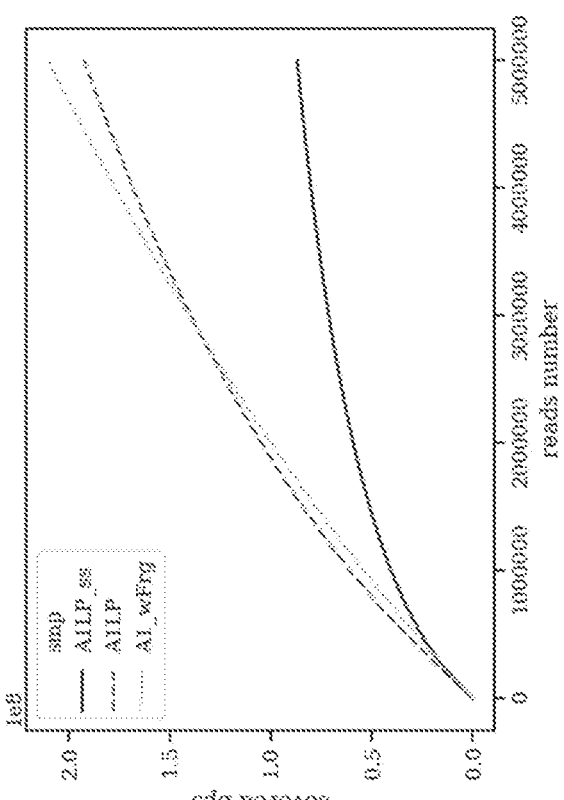

FIG. 2 shows the effect of the reduced genome representation on the observed coverage. FIG. 2A shows MseI fragment length distribution according to 3 different approaches: Amplil LowPass for Ion Torrent with size selection collecting fragments between 300 and 450 bp (A1LP_ss), Amplil LowPass with the selection derived by the sequencing step (A1LP) and libraries obtained after Amplil WGA followed by a random fragmentation and sequencing (Al_wFrg) (Binder V et al. 2014). These 3 different approaches represent a different level of reduction of genome representation, from the most stringent A1LP_ss up to Al_wFrg characterized by the absence of selection. FIG. 2B shows Lorenz curves obtained with the different approaches which show a gradual decrease of coverage uniformity with size selection level. The lower A1LP_ss uniformity can be explained by saturation of the DNA templates and the recurring sequencing of same fragments. The template saturation is confirmed by plots in FIGS. 2C and 2D, which show the total amount of covered bases and mean coverage per base respectively at incremental intervals of mapped reads. These plots clearly show that the size selection step (A1LP_ss) reduces the amount of DNA available with the effect of a limited covered target but with a higher coverage.

Figure 3:
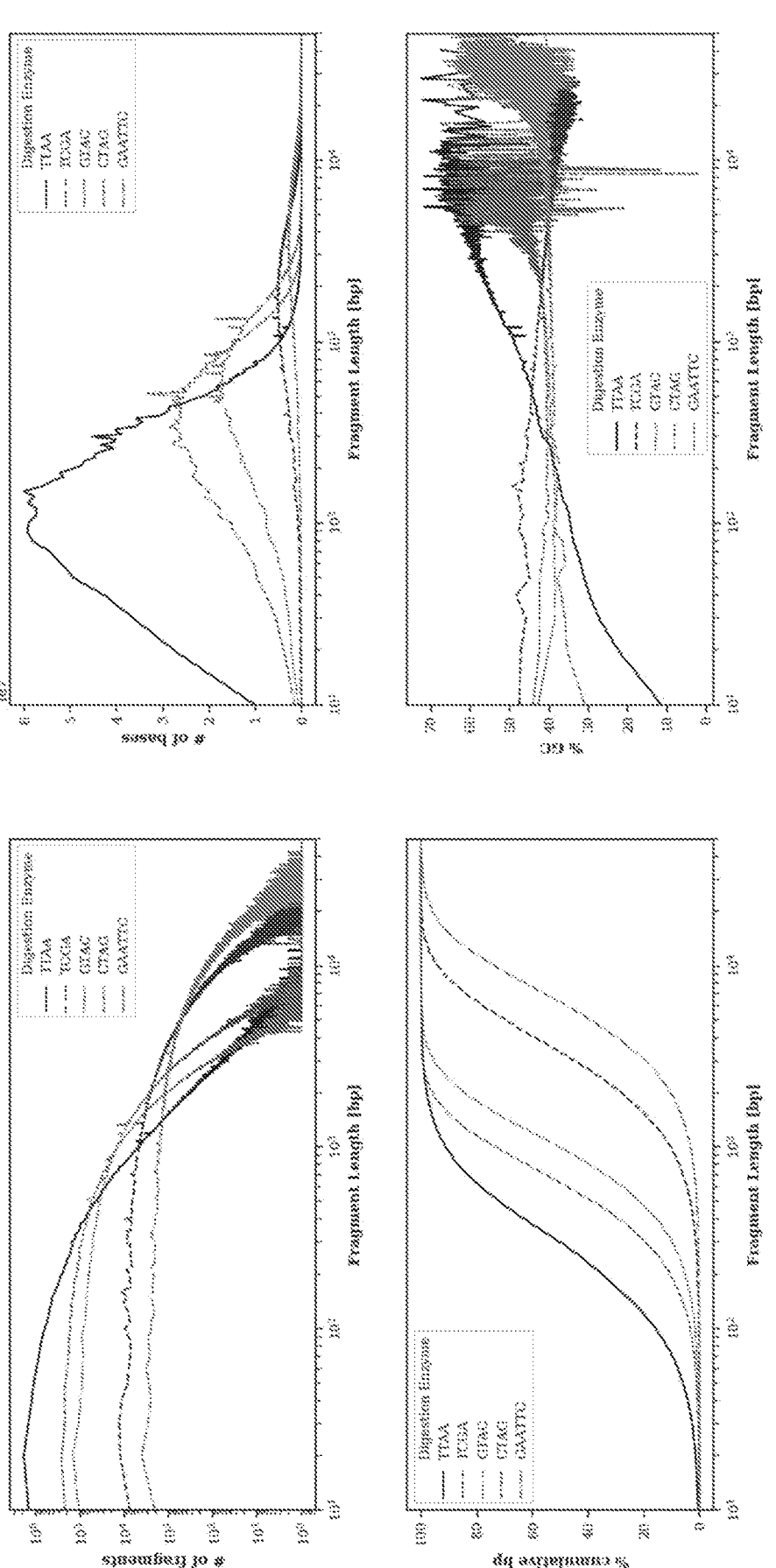
FIG. 3 shows graphs of in-silico digestion of human genome at different Restriction Sites.

It is worth noting that, the approach is flexible in that, different deterministic enzymes may be suitable depending on the desired resolution and/or sequencing platform and sequencing protocol used. For example, different frequent cutters may be used. In the examples of Amplil WGA, the TTAA motif is the Restriction Site. Other four-base cutters may be used to cut at different Restriction Site, such as GTAC, CTAG, (FIG. 3), obtaining a different distribution of fragments. FIG. 3 shows in-silico digestion of human genome with different Restriction Sites (four or six base pairs). For a given range of fragment lengths (e.g. suitable for a certain sequencer and size selection method), different restriction sites yield a different number of fragments.

When the DRS-WGA is first purified after the primary PCR, a first size-selection occurs, whereby shorter fragments of the WGA are removed along with free primers. Advantageously, the method uses a further step of selection. This additional step of selection can be achieved by either size-selecting certain fragments from the primary WGA and/or generating the massively parallel sequencing library by a method which restricts the sequenceable fragments. For example, Amplil LowPass kits include an inherent size selection step which is sufficient to positively impact the process. In WO2017/178655, a size selection on a gel is carried out. In WO2019/016401, successive steps of purification using SPRI-beads effectively produce a first size selection, whereby the length of base-pairs is restricted to a range substantially depending on the SPRI-beads concentration. In addition, the sequencer may also introduce a size selection per se, as longer fragments will generate sequence data with lower and lower efficiency (e.g. due to emulsion PCR efficiency in Ion Torrent, or bridge PCR for cluster formation in Illumina platforms).

In DRS-WGA there is also a deterministic relationship between the average size of the sequencing library and the subsampling ratio of the reference genome.

An in-silico analysis, carried out on the TTAA digest of the human reference genome hg19 (FIG. 4), yields a total of about 19M fragments including all chromosome sequences, which would translate to 38M fragments on a normal diploid human genome. By way of example, selecting in-silico, fragments in the range 175-225 bp will be only 1,252,559, covering approximately a total of 248M bases out of 3.09B bases, i.e. 8.02% of the human reference genome. See Table 1 below, in which number of fragments, total base-pairs and reduction ratio (%) are listed for different ranges of selection by size. This subsampling can be designated the Reduction Ratio (RR).

TABLE 1

| Spacing between fragments | | | |
| --- | --- | --- | --- |
| Range | N. Fragments | Tot. bps | Reduction Ratio |
| 75-125 | 3,057,163 | 298,482,600 | 9.64 |
| 175-225 | 1,252,559 | 248,367,191 | 8.02 |
| 275-325 | 703,011 | 210,389,610 | 6.80 |
| 375-425 | 390,419 | 155,603,924 | 5.03 |
| 475-525 | 217,861 | 108,653,407 | 3.51 |
| 725-775 | 68,581 | 51,428,399 | 1.66 |
| 975-1025 | 24,091 | 24,070,638 | 0.78 |

Figure 5:
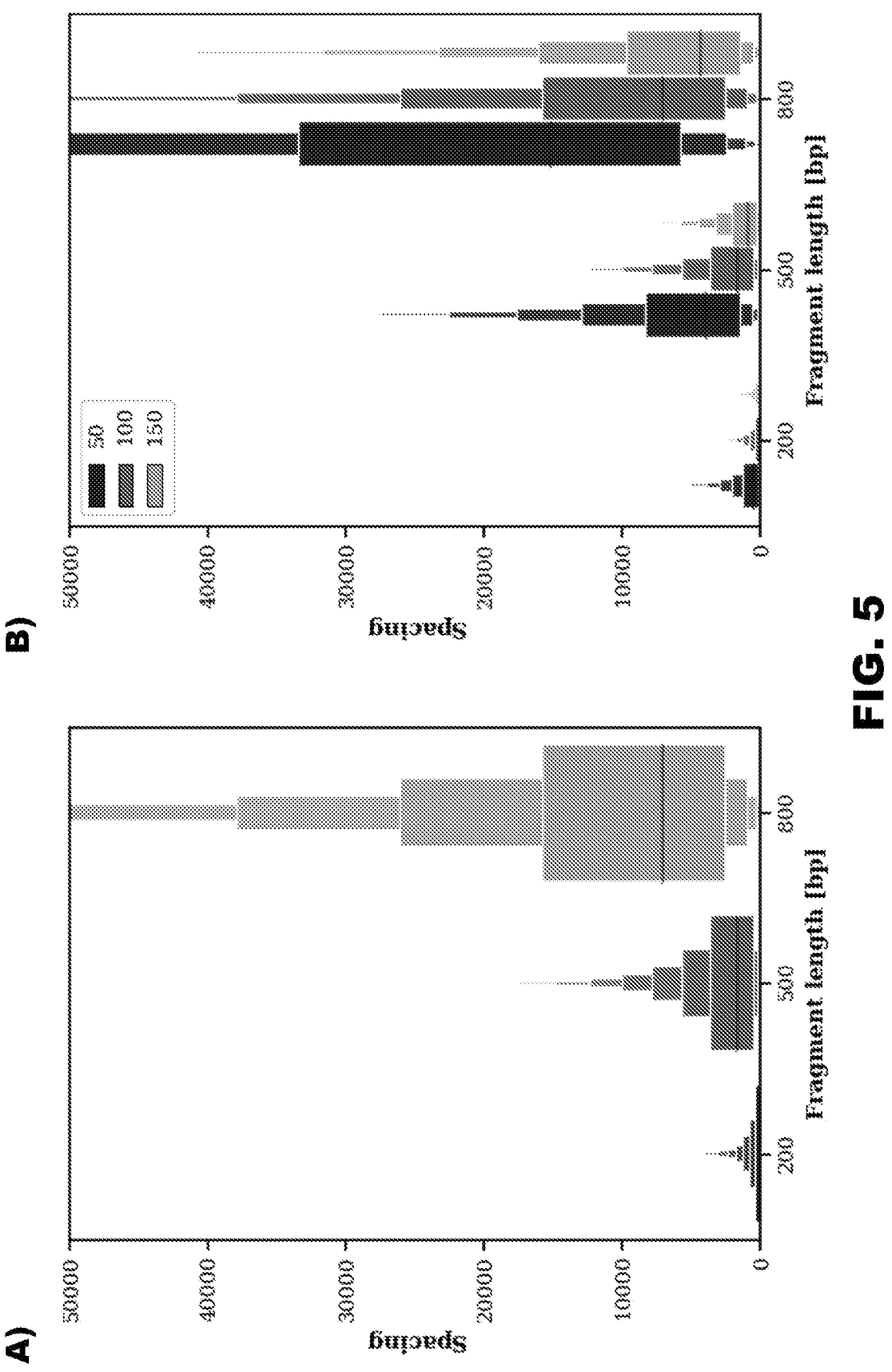
FIG. 5 shows the relationship between spacing and size of fragments selected for sequencing.

Along with the reduction ratio, in DRS-WGA there is also a defined relationship on the average spacing between successive fragments depending on the portion of the fragment length distribution selected for sequencing. In this connection, see FIG. 5, in which panel A shows positive correlation between fragment length and spacing, due to the decreasing number of fragments selected, measured for three different fragment size 200, 500, 800 with a band of ±100 bp; and panel B shows that, for each fragment size, three different bands (±50, ±100, ±150) were used for demonstrating the inverse correlation between band size and spacing, still due to the decreasing number of fragments obtainable with narrower ranges of size.

In general, by in-silico analysis of the human reference genome hg19 with regard to Amplil DRS-WGA fragments distribution, it is found that:

the higher the average base-pair length of fragments selected, the smaller the number of fragments, and the higher the spacing between them;

the narrower the range of fragments selected, the smaller the number of fragments, and the higher the spacing between them.

Size Selection of Fragments

Figure 4:
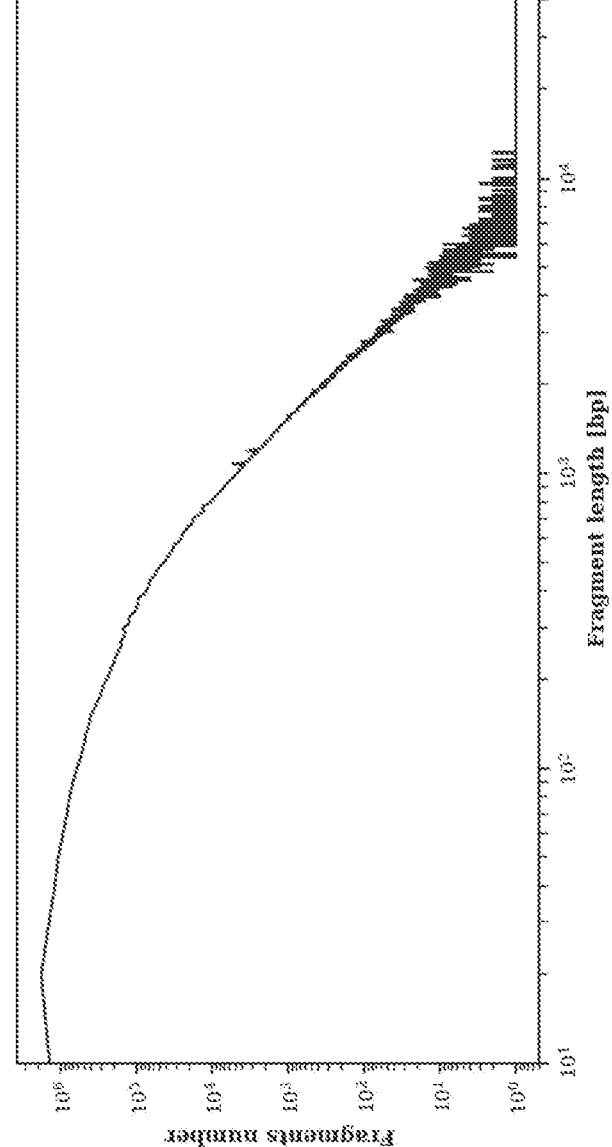
FIG. 4 shows in-silico analysis of number of DNA fragments as a function of fragment length obtained digesting the hg19 human genome with Amplil DRS-WGA enzyme (MseI).

Different size-selection techniques may also be used to achieve the desired Reduction Ratio, depending on the elected number of sequencing reads per sample and/or resolution. With reference to FIG. 4, it is clear that—for a given average fragment length—smaller or larger number of total fragments can be obtained selecting a respectively smaller or larger band centered on that average fragment length.

Instruments like the Pipping prep (Sage Science) may be used to have a tighter control on the fragment length distribution and, using an analogy to passband filters, also in having higher Q factor defined as $Q=Fcenter/DeltaF=[(Fmin+FMAX)/2]/(FMAX-Fmin)$ where $Fcenter=(Fmin+FMAX)/2$ is the average size of Fragments $DeltaF=FMAX-Fmin$ is the width of the range of fragment sizes Fmin is the size of fragments below which fragments are represented at a conventional relative level (e.g. $^1\!/_{10}=10\%$) or less with respect to the normalized, in-band, peak number of fragments per bin.

FMAX is the size of fragments above which fragments are represented at the same conventional relative level or less with respect to the normalized in-band peak number of fragments per bin.

With Illumina sequencing, the sequencing mode is preferably paired end sequencing, as the covered genome increases and thus the number of loci per-million read-pairs increases, augmenting the resolution. However, when the size selected for sequencing gets below a certain size, the paired-end sequencing will not increase the coverage as the two paired reads overlap completely.

With Ion Torrent sequencing, higher read lengths will proportionally increase the covered genome and thus the number of loci per-million reads increases, augmenting the resolution. In the Amplil LowPass IonTorrent kit (Menarini Silicon Biosystems), the barcoded pooled samples are size selected, on a gel or with other methods like Pippin Prep. The choice of different Q factor and average fragment length can provide different resolutions on a per million reads basis.

One advantage of pooling the samples and size-selecting the library for sequencing thereafter is that all samples will have the same distribution of fragment lengths, and in turn this will maximize the overlap of covered genome across different samples. This is relevant when using an approach based on controls (e.g. normal control or maternal control) to identify the potential heterozygous loci in the sample under test (SUT).

On the other hand, when using the Amplil LowPass kit for Illumina, the different LowPass libraries are at first size-selected and then pooled obtaining slightly different size-selections across different samples, thus reducing the covered genome across different samples on a per-Million reads basis. A size-selection after library pooling, although not mandated by the standard protocol, may be employed to increase the overlap across samples, which may be beneficial in analysis based on controls.

According to the present invention, the combination of DRS-WGA and LPWGS unexpectedly leads to a reduced representation from the input sample. By sequencing with NGS, this reduced representation library of the reference genome, in turn shrinks the covered genome in the selected (or any way sequenceable) base-pair range, and an effectively higher coverage for the covered genome on a per-Million reads basis is obtained, as compared to alternative WGA methods using random priming or random shearing.

This effect can be exploited according to the invention in different ways, depending on the situation.

An example is the availability of one or more control samples—such as "matched normal" and availability of one or more samples under test (SUT), such as a tumor sample. In this case, DRS-WGA increases the overlap of reads between SUT and control.

Another example is a control-free situation as is the case of pre-implantation genetic screening (PGS), where there is only availability of a single sample corresponding to the SUT. In this case, DRS-WGA increases the number of loci covered by more than one read.

Preferably, the library preparation from the DRS-WGA is one of the methods disclosed in WO2017/178655 and WO2019/016401, as the resulting reduction ratio is higher as opposed to digesting the WGA adaptors, fragmenting the DNA, and creating a sequenceable library thereafter, as carried out in Binder V. et al., 2014, or Hodgkinson C. L. et al., 2014. In fact, the DNA shearing increases the number of possible different fragments of the original DRS-WGA that can be found in a given base pair range selected for sequencing, because—once fragmented—longer fragments will fall back in the above said range, whereas only a fraction of the primary WGA fragments natively in-range will be kicked out of range due to the fragmentation, as smaller fragments tend to shear less efficiently with respect to longer fragments (see FIG. 2).

LoH Analysis

With reference again to FIG. 1, the massively parallel sequencing library is preferably obtained using Amplil Low-Pass kit (for Ion Torrent or for Illumina). The sample is sequenced using a compatible sequencer. The sequenced reads obtained from said library are mapped to the reference human genome and the alleles present in known and/or polymorphic loci are extracted. Preferably, such loci are covered by at least 2 sequencing reads. It should be noted that the detection of a single allele does not necessarily imply a real homozygous genotype, but may be a result of the low sequencing coverage. Said plurality of loci is preferably subdivided in genomic windows according to different criteria of genome partitioning. This partitioning is optional as in certain embodiments one may be interested only in the analysis of one or few predetermined genomic windows, for example a single chromosome or a single genomic locus comprising one or more genes of interest. The allelic status of loci detected in genomic windows is used to obtain a measurement. Such measurement, hereafter named LoH score, can be obtained by a variety of methods according to the invention, such as counting the number of heterozygous loci in the genomic window, or calculating the proportion of heterozygous loci. Moreover, a statistical test is preferably applied to determine the significance of heterozygous loci drop in correspondence of LoH events by comparison with either an internal control or by using an external control (from the same individual/s or from a different individual/s). Alternatively, a statistical test is preferably applied to determine the significance of heterozygous loci over-representation, in correspondence of genomic regions not in LoH, with respect to what expected based on sequencing and WGA error rates. Finally LoH score thresholding, based on a fixed threshold calculated from a training dataset with known LoH events, is preferably applied to define genomic regions corresponding to LoH events. Single steps of the method are detailed in the following.

Genome Partitioning

With reference to FIG. 1, the optional step of partitioning may be carried out in three alternative manners:

i) constant base-pair genomic windows
   ii) constant number of loci windows
   iii) copy-number segments.

Figure 6:
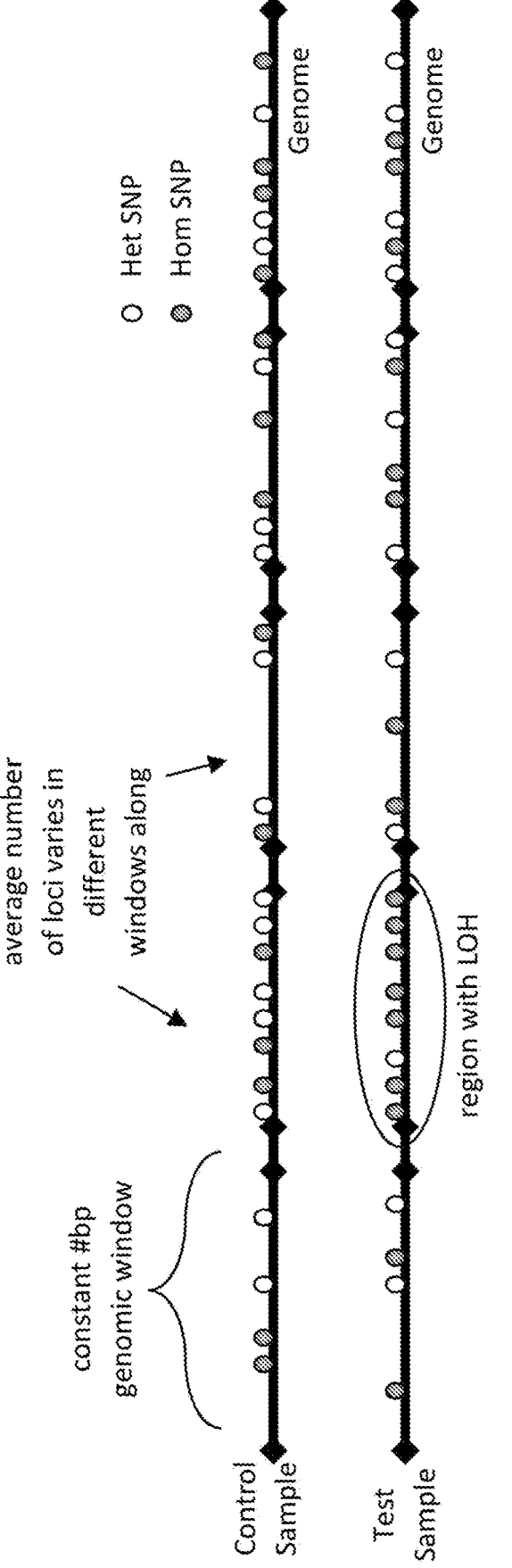
FIG. 6 shows a schematic representation of an example of partitioning based on constant base-pair genomic windows.

In alternative i), which is shown in FIG. 6, the genomic window has a constant width. Each genomic window contains a plurality of loci, the number of which depends on the genomic location. This approach may be advantageous when comparing a sample against a set of control normal samples as the reference genome is partitioned in the same way in all the samples, thus allowing a direct comparison of the LoH score for each genomic window across multiple samples. As the number and proportion of heterozygous loci detected in a genomic window of defined width will increase at higher read depths, to allow the comparison of a sample against a control (or multiple) control samples, the number of mapped reads in each sample is preferably normalized to a fixed number of reads. Such normalization is performed by randomly sampling reads, mapped to the reference genome, until the desired number is reached. The normalized number of reads may be, for example, 1 million or 2 millions of reads, preferably 3 millions, 4 millions, 5 millions, 6 millions, 7 millions, 8 millions or 9 millions of reads.

FIG. 6 shows a schematic representation of an example of partitioning based on constant base-pair genomic windows. Paired control (top) and test (bottom) samples are represented. A continuous line represents (a portion of) the genome. Diamond markers delimit genomic windows of constant width and known polymorphic loci are represented by dots (heterozygous loci: white filled dots; homozygous loci: grey filled dots). The number of loci detected per genomic window varies across the genome but is expected to be similar, on average, for a given window, between two different samples the total read mappings of which have been normalized to a defined read count. A genomic window in LoH in a test sample is expected to show a drop in heterozygous loci compared to the same window in a normal control sample. The same window cannot be directly compared with genomic windows located on different genome positions on the same (or other) sample because of the bias in SNP densities along the genome.

Figure 7:
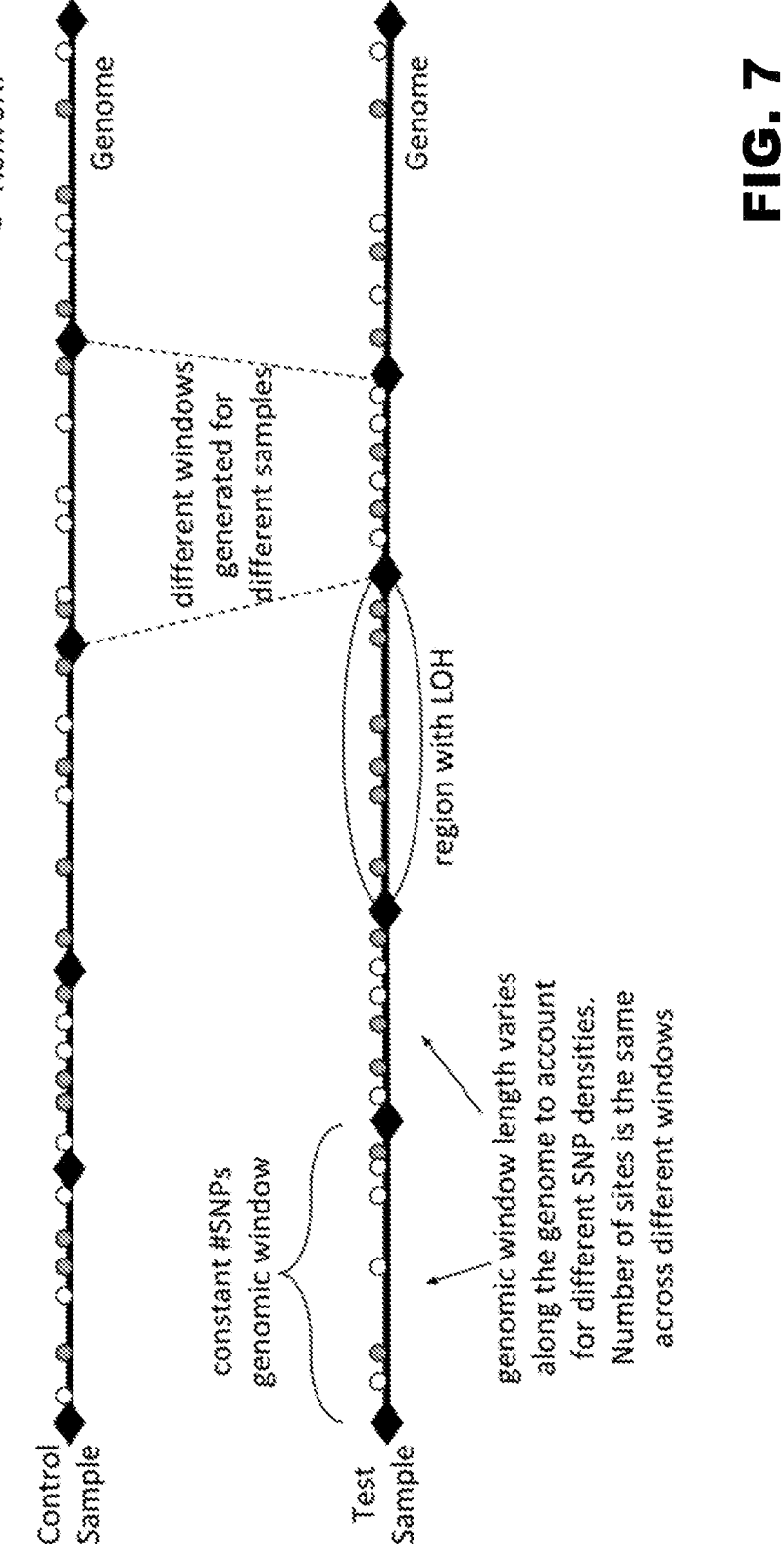
FIG. 7 shows a schematic representation of an example of partitioning based on constant number of loci per window.

In alternative ii), which is shown in FIG. 7, the genomic window has a constant number of loci. This approach allows to normalize the LoH score for different SNP densities across the genome. The method may be advantageous when using a control-free approach as it allows, for example, to apply the same threshold for all genomic windows irrespectively of their position in the genome and of their underlying SNP density. The method may be disadvantageous when comparing the test sample to control samples as different genomic windows may be generated for different samples depending on the distribution of loci sampled and detected by low-pass sequencing.

FIG. 7 shows a schematic representation of an example of partitioning based on constant number of loci per window. Paired control (top) and test (bottom) samples are represented. A continuous line represents (a portion of) the genome. Diamond markers delimit genomic windows containing a constant number of loci. Known polymorphic loci are represented by dots (heterozygous loci: white filled dots; homozygous loci: grey filled dots). Because of the low sequencing coverage not all loci in a genomic region will be detected. Thus, genomic window ends can vary between different samples based on loci sampling by sequencing reads and, as such, genomic windows detected in a test sample are not directly comparable to corresponding genomic windows in other (control) samples. A genomic window in LoH in a test sample is expected to show a drop in heterozygous loci with respect to genomic windows of the same sample which are not in LoH.

Figure 8:
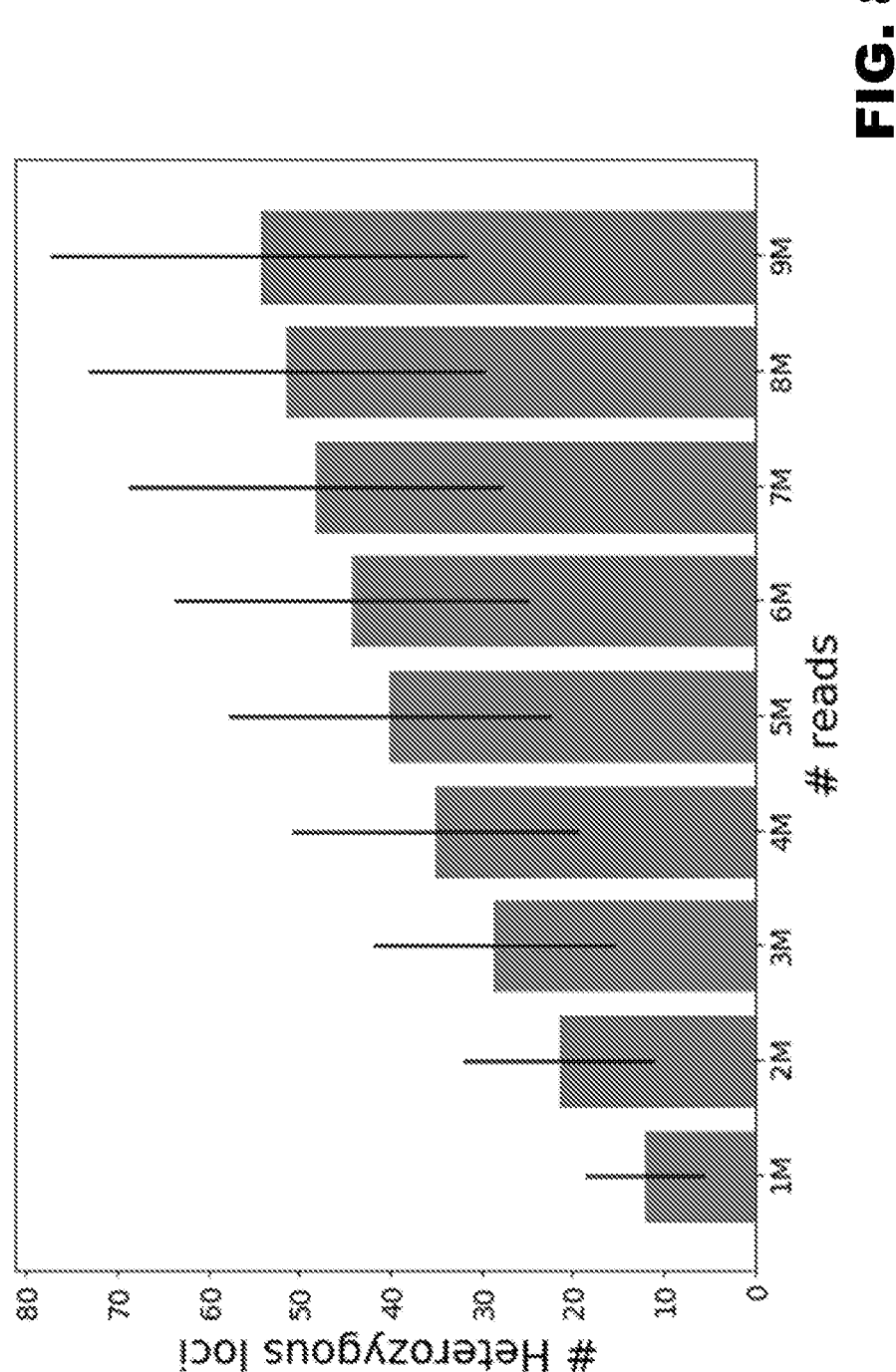
FIG. 8 is a graph showing the mean number of heterozygous loci detected in genomic windows of n=1000 SNPs at different number of reads (1 to 9 millions). Vertical black lines show the standard deviation from the means.

The number and proportion of heterozygous loci detected in a genomic window with a constant number of loci will increase at higher read depths (see FIG. 8). Preferably, to allow the thresholding of the LoH score to a precomputed value, the number of mapped reads in each sample is normalized to a fixed number of reads. Such normalization is performed by randomly sampling reads, mapping to the reference genome, until the desired number is reached. The normalized number of reads may be, for example, 1 million or 2 millions of reads, preferably 3 millions, 4 millions, 5 millions, 6 millions, 7 millions, 8 millions or 9 millions of reads.

Figure 9:
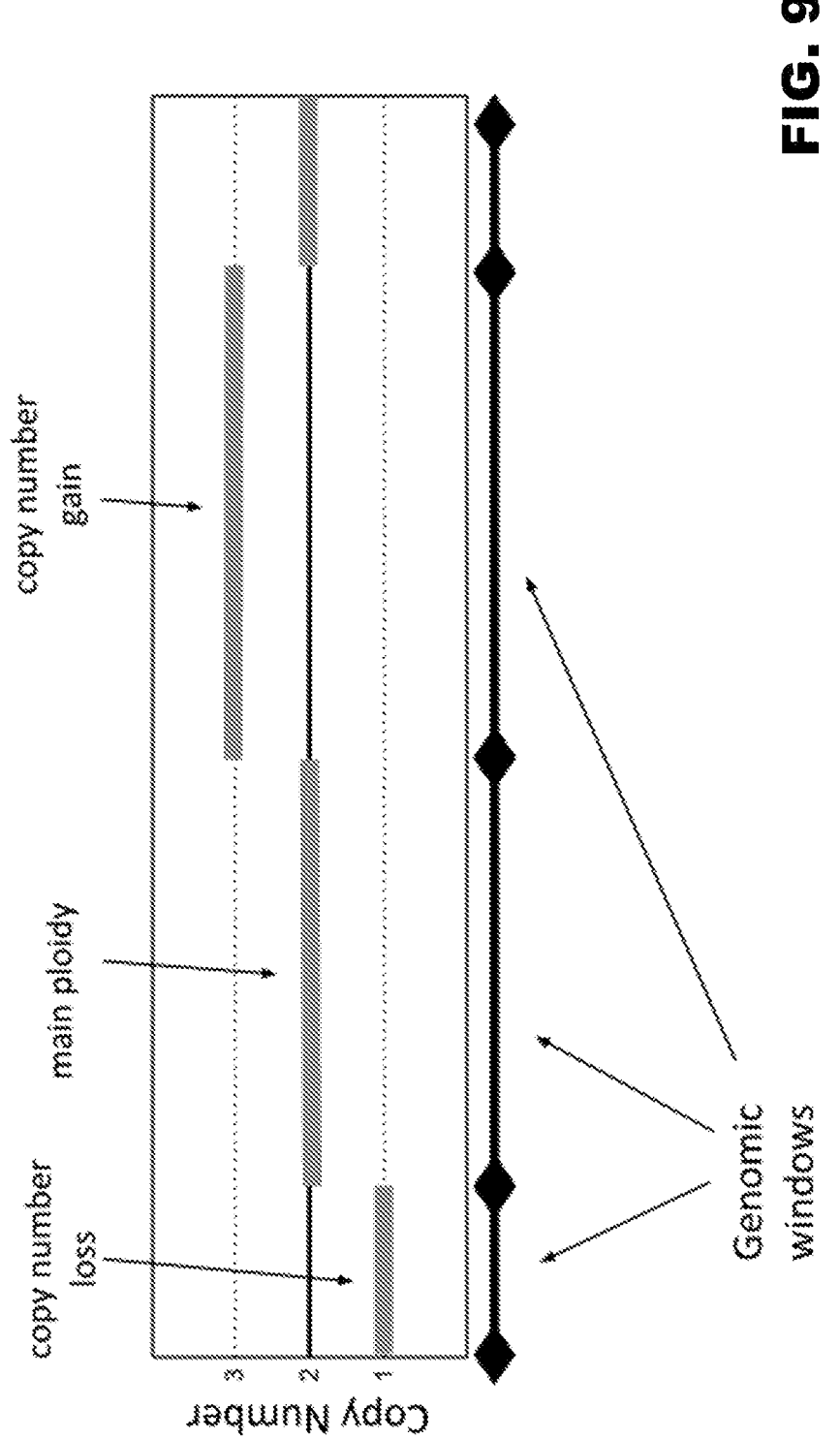
FIG. 9 shows a schematic representation of partitioning based on copy-number segments.

In alternative iii), which is shown in FIG. 9, the genomic window is a segmented genome region between two copy number breakpoints, contained in a chromosome arm, which may be defined by normalizing raw copy number counts in genomic windows by GC-content (Boeva, V. et al., 2011, Bioinformatics, 27(2), 268-269) and by applying a segmentation algorithm such as a LASSO-based algorithm (Harchaoui, Z. et al., 2008, Adv. Neural Inform. Process. Syst., 20, 617-624), circular binary segmentation (CBS) (Seshan V E. et al., 2019, DNAcopy: DNA copy number data analysis. R package version 1.58.0) or similar algorithm to normalize read counts. This method is based on the assumption that a genomic region showing a copy number level change, with respect to sample main "normal" ploidy, has likely been affected by a single genomic copy-number aberration event and thus is expected to have a uniform LoH status. Compared to alternatives (i) and (ii), genomic windows defined by this method are generally much larger (up to 2-3 orders of magnitude) and will contain a larger number of known heterozygous and/or polymorphic loci, thus allowing to get a higher statistical power. Moreover, by combining 2 different biological dimensions (copy-number, LoH score), more accurate results, with lower false positive rate, can be achieved with this method. The method however may be disadvantageous in case of small LoH events located into larger copy number events which would remain undetected with this method. As it is not infrequent that a chromosome arm undergoes an LoH event followed by a duplication, preferably chromosome arms will be used as segmentation unit in chromosomes without copy number changes. This prevents the miscall as LoH of a shorter chromosome arm when only the longer arm is affected (false-positive), or in the dual case, the miscall as no-LoH for the shorter chromosome arm when only the shorter is affected (false negative).

More in particular, FIG. 9 provides an exemplary representation of the copy number profile of a chromosome arm (genome main ploidy=2) which has been affected by two copy number change events: a copy number loss segment with a copy number=1; a copy number gain with a copy number=3. Genomic windows are defined as the regions between 2 consecutive copy number breakpoints.

Segmentation may also be employed leveraging copy-number information to exclude false positives deriving from high-level amplifications. In fact, a high-level amplification most probably derives from a single allele, and thus introduces a bias in the allelic representation in the region, whereby the minor allele, even if present, will be under-represented and may induce a false-positive LoH call.

Table 2 below shows the main features and pros and cons of each alternative step of partitioning according to the present invention.

TABLE 2

| Genome partitioning | Features | Pros | Cons |
|---|---|---|---|
| (i) | Genomic windows have the same length across the genome and across different samples. Different loci density along the genome, resulting in genomic windows with different number of loci. | Easy to apply in test-vs-control cases | Dependent on loci density Not easily applicable to a control-free setup |
| (ii) | Independent from loci density variation along the genome | Applicable to control-free setup | Test vs control not applicable |
| (iii) | Assume that copy- | Takes into | Potentially |

TABLE 2-continued

| Genome partitioning | Features | Pros | Cons |
|---|---|---|---|
| | number segments are likely to have the same LoH status | account copy-number profiles information Higher statistical power | small false negative events in larger copy-number segments |

LoH Scoring

Step g. of assigning an LoH score to at least one genomic window of said reference genome for said at least one sample as a function of the number of loci with at least two different alleles in said plurality of loci also involves alternative preferred embodiments.

In one preferred embodiment, the LoH score corresponds to the number of heterozygous loci in said at least one genomic window. A genomic window in LoH is expected to show a scarcity of heterozygous loci compared to regions or samples which are not in LoH (see FIG. 10).

Figures 10, 11:
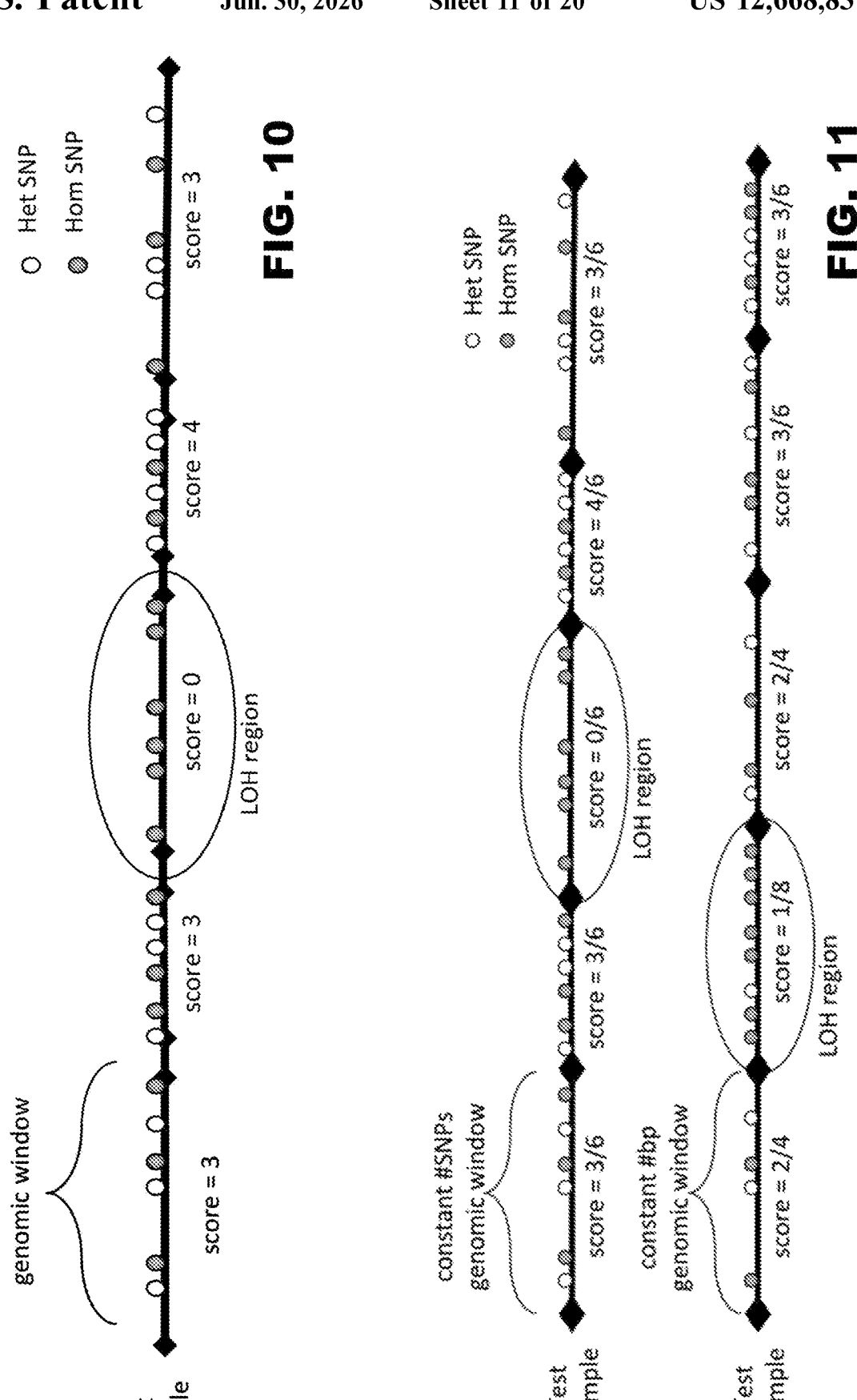
FIG. 10 shows the case in which the LoH score is defined as the number of heterozygous loci.
FIG. 11 shows the case in which the LoH score is defined as the proportion of heterozygous loci over total loci in genomic windows with constant number of loci.

In another preferred embodiment, for each genomic window, an LoH score is defined as the proportion of heterozygous loci detected in that genomic window with respect to the total number of polymorphic loci in the same genomic window (FIG. 11). Similarly to the method above, a consistent reduction of the LoH score is expected in the presence of an LoH event. This method may be advantageous when the windows do not contain an homogeneous number of loci detected, for example when a constant base-pair genomic window is used or copy number segments are used to partition the genome.

LoH Scoring—Statistical Test

Preferably, for each genomic window an LoH score is defined by the results of a statistical test on the frequency of biallelic loci observed.

In a preferred embodiment, the significance of under-representation of heterozygous loci with respect to an internal/external control can be assessed by performing a statistical test. In detail, a contingency table is built for each genomic window considering the two following classifications: 1) sample type (test, control); 2) loci type (heterozygous, homozygous). A statistical test, such as the Fisher Exact test or comparable test for the analysis of contingency tables (e.g.: chi-squared test, G-test, Barnard's exact test, Fisher-Freeman-Halton test) is then applied. Preferably, the statistical test should be performed one-sided in order to restrict the detection to the case where there is an under-representation of heterozygous loci due to LoH. In fact, when in a given genomic segment there is a gain, i.e. an increase of copy-number, there is an increase in the number of reads using Low-Pass WGS. This may result in a higher number of heterozygous loci in the absence of LoH, and may be flagged as significant by a two-sided statistical test, but for the opposite reason of the objective of the analysis.

In an alternative preferred embodiment, the significance of over-representation of heterozygous loci with respect to that expected from sequencing and WGA error rates can be tested. This approach may be of advantage when testing for 'gain of heterozygosity' (hereinafter GoH) in haploid single-cells, such as gametes. This may occur for example due to errors in unbalanced disjunction during meiosis resulting in a gain of a chromosome.

Given the large number of tests performed for each experiment (about 200, 400, 600 for a 1 million reads sample with fixed windows of 500, 1000 and 1500 SNPs), a multiple testing correction may be applied (see for example Benja-mini Y. et al., 1995, Journal of the Royal Statistical Society. Series B (Methodological) Vol. 57, No. 1:pp. 289-300). The LoH score is then defined as the p-value resulting from the statistical test.

Control Sample

The control may be "internal" and can be defined, for example, by considering the genomic regions with ploidy equal to the likeliest main (average) genome ploidy. This approach assumes that most genomic regions not showing copy number alterations are not in LoH.

Alternatively, the control may be "external" and can be generated for example by using one or multiple normal samples from the same individual under test or from different individuals.

The use of an internal control may be advantageous for diploid or polyploid samples (e.g.: tumor samples) as it is independent of the number of reads (does not require normalization of the number of mapped reads) and in case of damaged samples (e.g.: FFPE samples). Indeed, damaged samples may show a higher occurrence of dropouts, in which one of the 2 alleles at a loci is lost because of DNA damage, compared to non-damaged ones and, thus, a lower number of heterozygous sites than expected for genomic regions not in LoH. This may hinder the comparison of test vs external control samples with different levels of damaging. By using an internal control, such bias is removed as control and test genomic windows will have the same level of dropout rate.

LoH Thresholding and LoH Calling

Optionally, the LoH score obtained from previous steps may be thresholded to define genomic regions in LoH. In most cases, the number and proportion of heterozygous loci detected in a genomic window with a constant number of loci will increase at higher read depths. To allow the thresholding of the LoH score to a precomputed value, the number of mapped reads in each sample is preferably normalized to a fixed number of reads. Such normalization is performed by randomly sampling reads, mapping to the reference genome, until the desired number is reached (preferably contained in the range going from 1,000,000 mapped reads to 10,000,000 mapped reads). The above considerations do not apply when the LoH score is calculated by performing a statistical test against an "internal" control.

Figure 12:
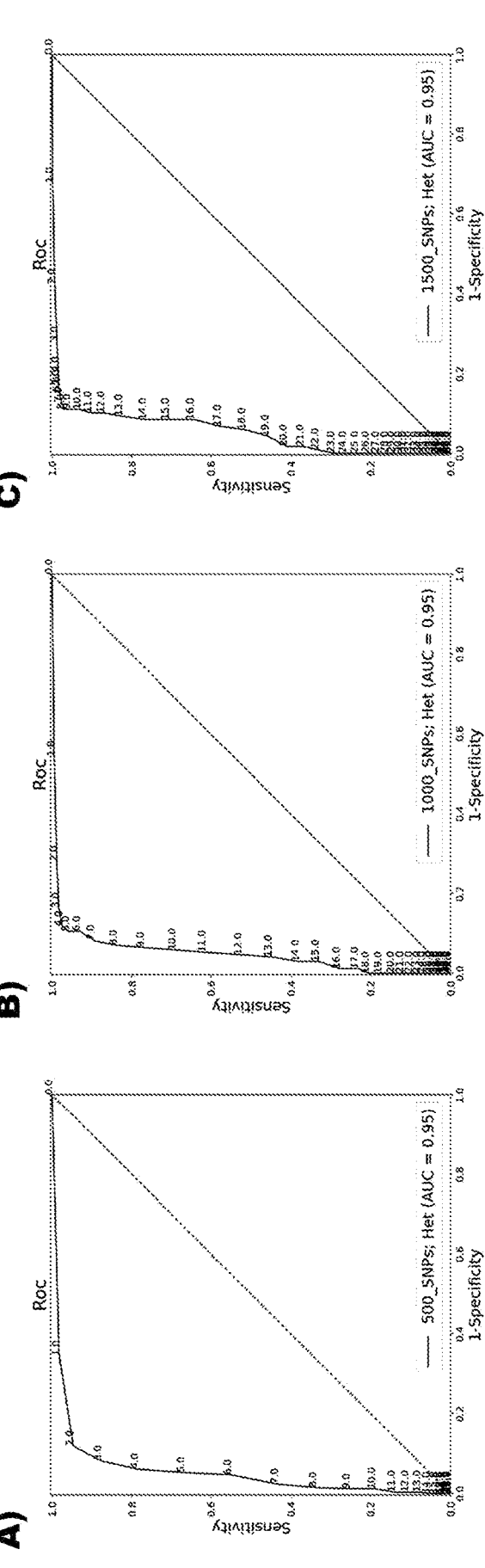
FIG. 12 shows the ROC analysis used for the definition of a LoH score threshold, defined as the number of biallelic SNPs in a window of (A) n=500, (B) n=1000, (C) n=1500 SNPs covered by at least 1 read with 1.000.000 mapped reads.

Preferentially, in the case of LoH score calculated as number of heterozygous loci, data is first downsampled to 1.000.000 mapped reads. Loci, covered by at least 1 read, are partitioned using windows with fixed number of loci detected (e.g. n=500; n=1000; n=1500). Some preferred threshold values are 3, 6, 9 heterozygous SNPs out of 500, 1000 and 1500 loci, respectively (FIG. 12). LoH is then called in a given genomic window if the LoH score is lower than the selected threshold.

More in detail, FIG. 12 shows ROC analysis used for the definition of a LoH score threshold, defined as the number of biallelic SNPs in a window of (A) n=500, (B) n=1000, (C) n=1500 SNPs covered by at least 1 read with 1.000.000 mapped reads. LoHs detected in the tumor cell by high pass whole genome sequencing and B-allele frequency analysis were used as reference.

In the case of LoH score calculated as p-value, resulting from the application of a statistical test, some preferred thresholds may be, for example, $5*10^{-2}$ or $1*10^{-2}$. LoH is then called in a genomic window if the LoH score is lower than the selected threshold.

Once LoH score has been thresholded, LoH status can be assigned to genomic regions according to different criteria described below.

1) LoH regions calling by merging windows. In this preferred embodiment, an LoH status is assigned to a genomic region if the LoH scores for each genomic window contained in that region pass the thresholding step.

2) LoH regions calling as a function of LoH status in the genomic windows. In this preferred embodiment, an LoH status is assigned to a genomic region if a given percentage/fraction of the genomic windows contained in that genomic region passes the thresholding step. As an example if more than 66%, 75%, 80%, 85%, 90%, 95% of the windows in a genomic region pass the thresholding step, an LoH status is assigned to that genomic region.

3) LoH calling in genomic regions comprising tumor suppressor genes. In this preferred embodiment, at least one genomic region comprises a tumor suppressor gene.

Preferably said gene is selected from the group consisting of BRCA1, BRCA2, PALB2, TP53, CDKN2A, RB1, APC, PTEN, CDKN1B, DMP1, NF1, AML1, EGR1, TGFBR1, TGFBR2, and SMAD4.

Sample Purity

LoH may be identified in a DNA deriving from a mixture of different kinds of cells (e.g.: tumor cells and normal cells). Sample purity is defined as the percentage of sample in the mixture which belongs to the type of interest (e.g.: tumor cells).

For example, when #TC tumor cells which are clonal, i.e. genomically identical and thus having the same pattern of LoH and CNAs are mixed with #NC normal cells from the same individual, the purity of the resulting sample will be #TC/(#TC+#NC) and will be homogenous across the genome.

Generalizing, by purity we mean here a concept relative to the LoH status in a given Region of Interest comprised of one or more Genomic regions. The Region of Interest may be as large as the entire reference genome (as in the previous example) or as small as a 100 kbp.

For example, in the presence of a pool of tumor cells representing different clones deriving from the same last common ancestor tumor cell, the purity may vary across different genomic regions from a minimum of 1/Number of cells in the pool—when an LoH region is represented in only one cell—to a maximum of 100%, when a Genomic region LoH status is common across all clones derived from the Last common ancestor.

Figure 13:
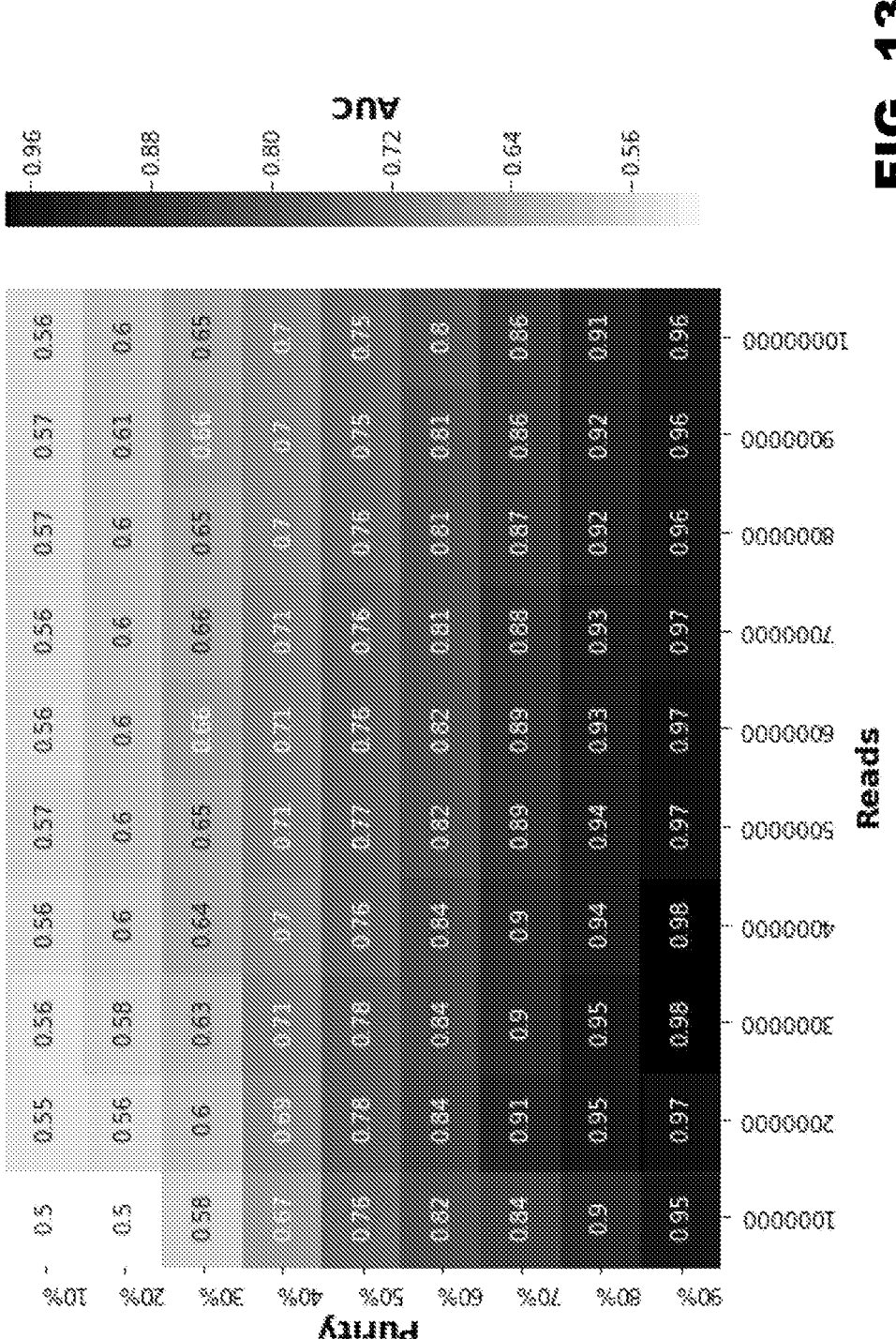
FIG. 13 shows receiver operating characteristic (ROC) area under curve (AUC) values for LoH score at different number of mapped reads (1.000.000-10.000.000 reads) and sample purity (10%-90%).

The sample analysed for LoH preferably has a purity of at least 50%, more preferably at least 70%, as can be appreciated from FIG. 13, which shows receiver operating characteristic (ROC) area under curve (AUC) values for LoH score at different number of mapped reads (1.000.000-10.000.000 reads) and sample purity (10%-90%). LoH score is defined as the number of heterozygous SNPs in a window of n=150 SNPs covered by at least 2 reads. Samples at different purities are obtained by mixing in silico reads obtained from the analysis of a tumor cell and a normal cell in proportions (tumor:normal) equivalent to the target purity. LoHs detected in the tumor cell by high pass whole genome sequencing are used as reference.

Effect of Size Selection on LoH Detection

As already mentioned previously, a size selection is preferably performed during or after step c. of preparing a massively parallel sequencing library. The size of the fragments may be chosen according to different criteria. The sequencing method may be chosen by different criteria, also depending on the fragment size. In general, the higher the number of loci (polymorphic or heterozygous) contributing to the LoH analysis the better is the resolution (per Million reads).

Figure 14:
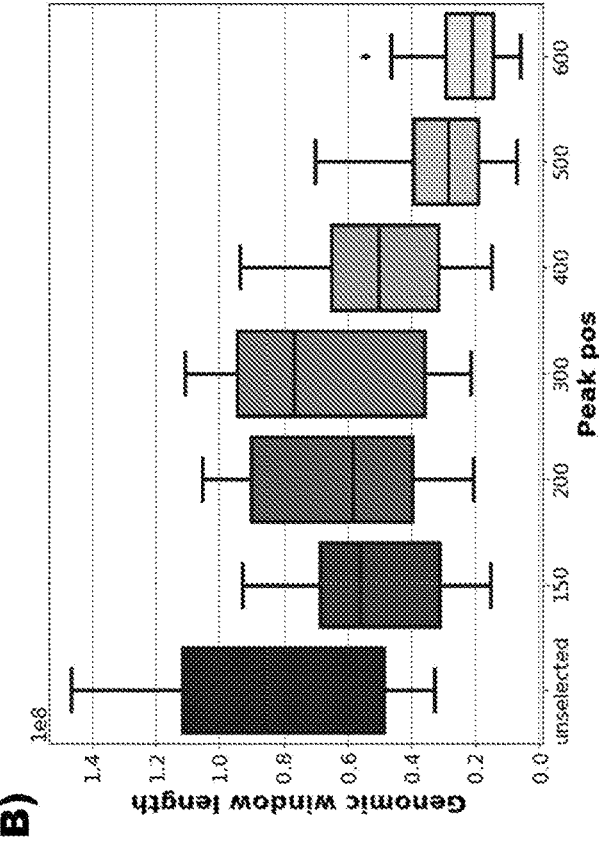
FIG. 14 shows data obtained from sequencing libraries prepared with Amplil LowPass for Illumina related to size selection of fragments.
Figure 14:
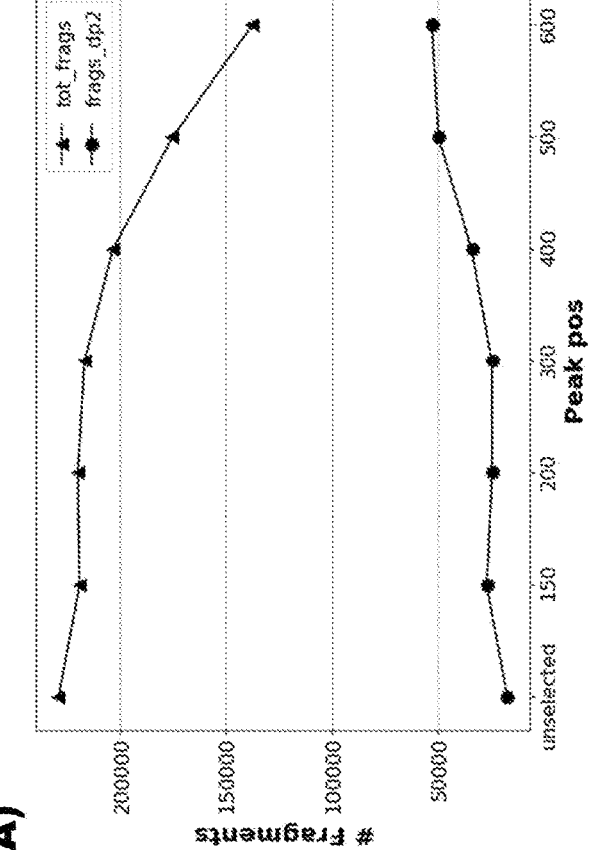
Figure 14:
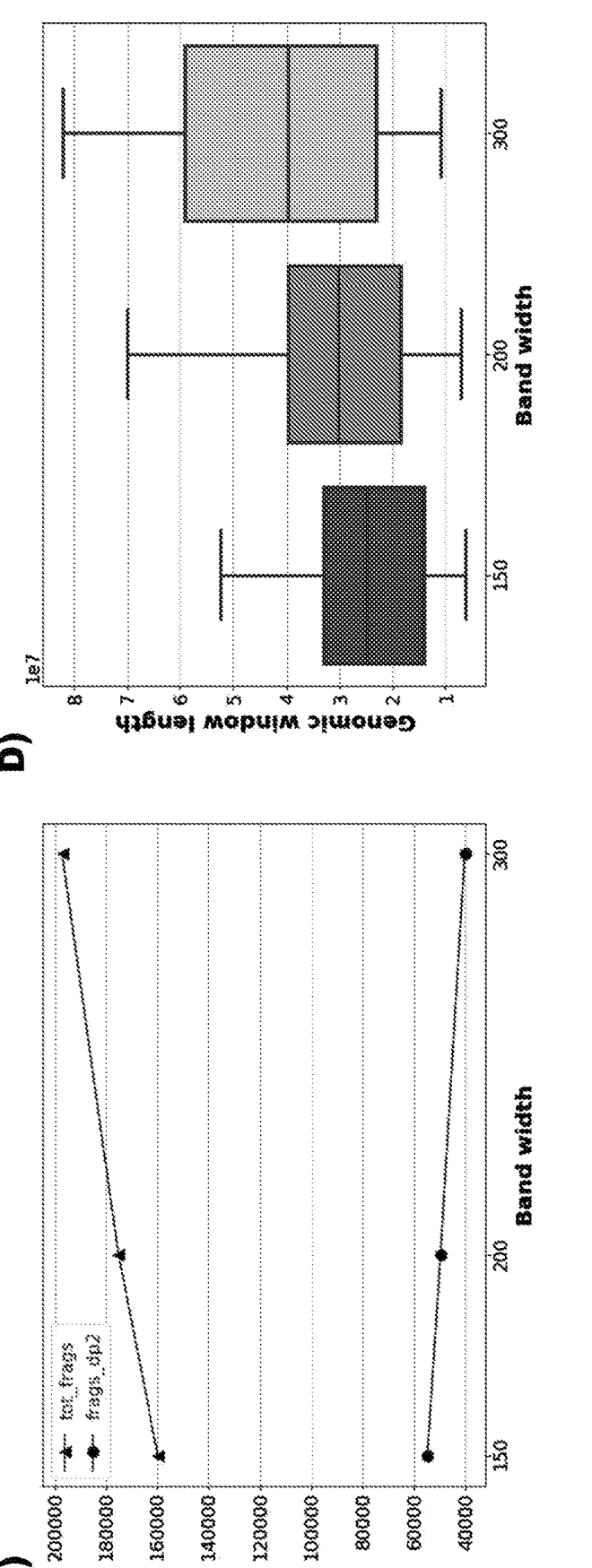
Figure 14:
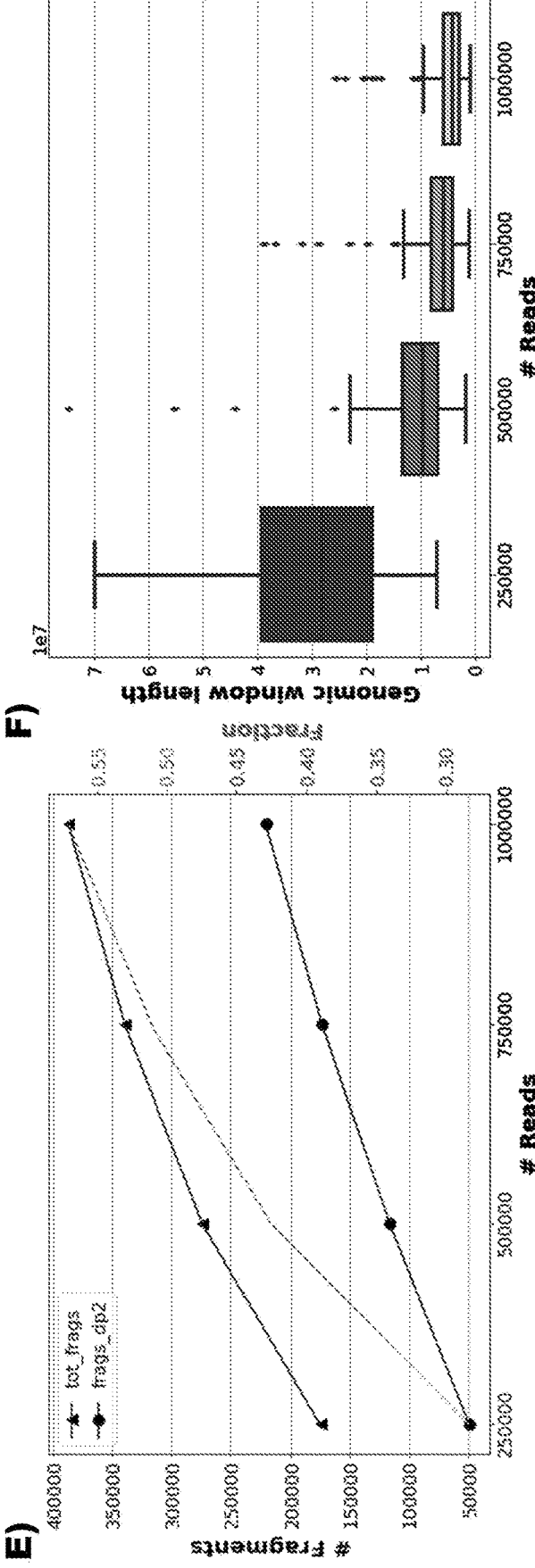

FIG. 14 shows data obtained by selecting in silico a subset of sequenced fragments from data obtained from a real single cell sample of increasing Fcenter (sequencing libraries prepared with Amplil LowPass for Illumina). FIG. 14A shows the effect of size selection (band width 100) on coverage of DRS-WGA fragments respect to fragments mean length, with 250.000 reads; FIG. 14B shows the effect of size selection (band width 100) on resolution in terms of base pairs (windows of 150 SNPs covered by at least 2 reads), with 250.000 reads; FIG. 14C shows the effect of size selection band width on coverage of DRS-WGA fragments at a fixed fragments mean length (500 bp), with 250.000 reads;

FIG. 14D shows the effect of size selection band width on resolution (bp) at a fixed fragments mean length (500 bp), with 250.000 reads; FIG. 14E shows the effect of number of reads on coverage of DRS-WGA fragments at a fixed fragments mean length (500 bp). The fraction of fragments covered by at least 2 reads and the total number of covered fragments increases in proportion to the number of mapped reads (dashed line); FIG. 14F shows the effect of number of reads on resolution (bp) at a fixed fragments mean length (500 bp).

These data show that the total number of DRS-WGA fragments decreases while the number of fragments covered by more than one read, useful to call SNPs, increases reaching a plateau at 500 bp (FIG. 14A). Resolution increases accordingly as shown by a decrease in length of genomic windows with fixed number of SNPs (n=150; FIG. 14B). When different bandwidths are applied to a given number of mapped reads and Fcenter, coverage of fragments and resolution increase at decreasing of bandwidth (Figure (14C and 14D). Resolution increases also with number of mapped reads (FIGS. 14E and 14F).

EXAMPLES

Table 3 below summarises the features of the methods used in 3 examples disclosed in the following.

TABLE 3

| Analysis method | | Example ID | | |
|---|---|---|---|---|
| | | 1 | 2 | 3 |
| Partitioning LoH Scoring Thresholding | Constant bp genomic window | X | | |
| | Constant number of loci | | X | |
| | Segments defined by copy-number | | | X |
| | Heterozygous number | | X | |
| | Heterozygous Proportion | X | | X |
| | P-value | X | | X |
| | Heterozygous number | | X | |
| | Heterozygous proportion | | | |

TABLE 3-continued

| | Analysis method | | Example ID | | |
|---|---|---|---|---|---|
| | | | 1 | 2 | 3 |
| Controls | P-value | | | | X |
| | Internal | | | | X |
| | External | | X | | |

Example 1

In Example 1, Amplil LowPass for Illumina DNA libraries of 1 circulating tumor cell (CTC; test) and 1 white blood cell (WBC; control) obtained from a male patient affected by Multiple Myeloma were considered. The sequenced reads were mapped to the hg19 reference human genome and downsampled at 1, 2, 3, 4, 5, 6, 7, 8, 9 million reads. The alleles present at dbSNP polymorphic loci (dbSNP150 common variants with a minor allele frequency $\geq$5%) were extracted from both libraries. Loci were partitioned with a fixed 10.000.000 bp genomic window. A one-sided Fisher exact test was employed to assess the significance of the association (Table 4) between the two kinds of classification, with the null hypothesis that heterozygous and homozygous loci are equally likely in WBC (control) and CTC (test).

TABLE 4

| | | sample type | |
|---|---|---|---|
| | | WBC (control) | CTC (test) |
| loci type | Het | number of loci heterozygous in control | number of loci heterozygous in test |
| | Hom | number of loci homozygous in control | number of loci homozygous in test |

Figure 15:
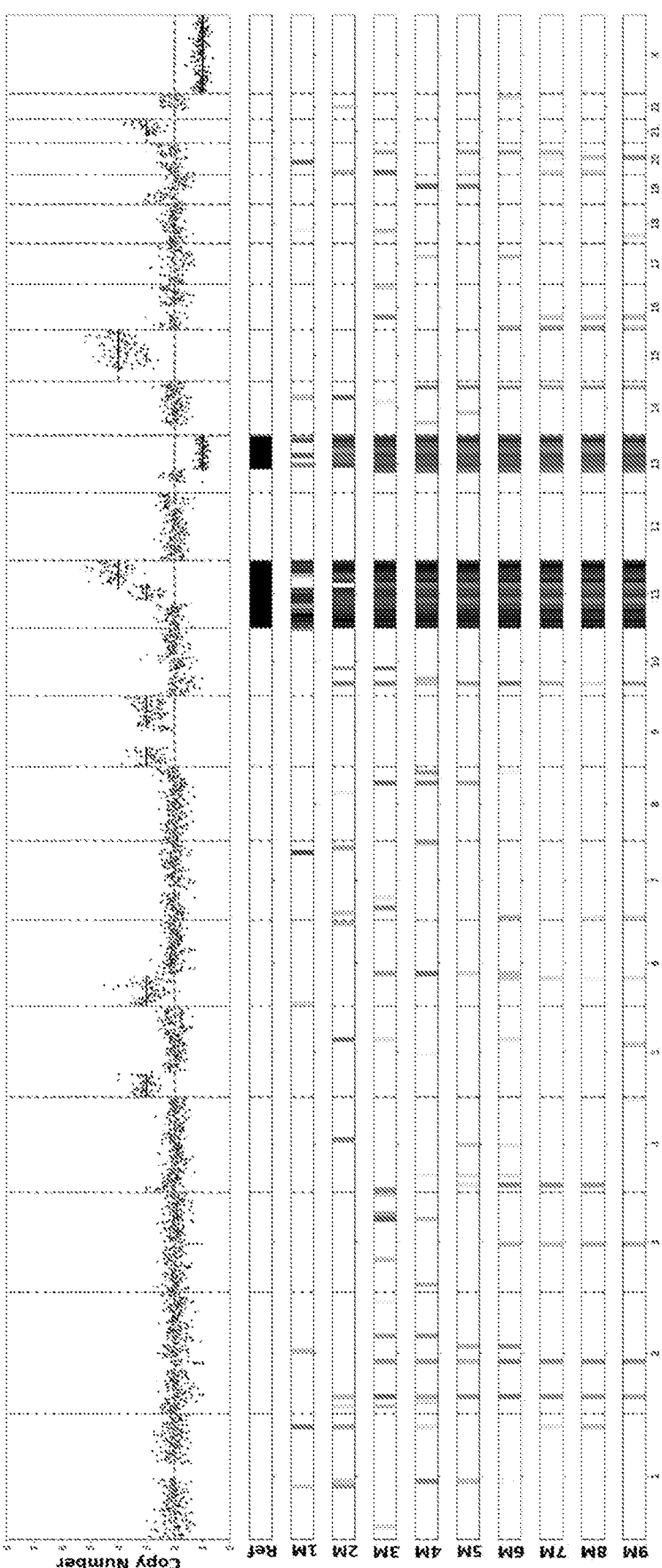
FIG. 15 shows an example of the detection of LoH by using constant base pair genomic windows and application of Fisher statistical test.

Results of the test at each downsampling level are shown in FIG. 15. Starting from 2 million reads the method shows a high sensitivity in detecting known LoH events on chromosomes 11 and 13.

In detail, FIG. 15 shows, on top, a copy-number plot of a CTC from a patient suffering from multiple myeloma. On the x axis are the chromosomes; on the y axis is the copy number. Each dot represents a genomic window of fixed size. Copy number segments are represented as solid lines. A reference (Ref) track is shown below the copy number plot, which represents known LoH regions detected by high pass whole genome sequencing of the same CTC are shown in solid black. Below are represented tracks marked with 1M to 9M: logged p-value (base=10) heatmaps of the results of the Fisher exact test at different number of reads (1 to 9 millions). More significant values are represented by a deeper shade of gray.

Example 2

In Example 2, the same single CTC data used in Example 1 is used as input and data is downsampled at 1 million reads. In this case loci were partitioned in windows with a fixed number (n=1000) of loci covered by at least 1 read. For the identification of LoH regions, the LoH score was calculated as the number of heterozygous positions in each window.

Figure 16:
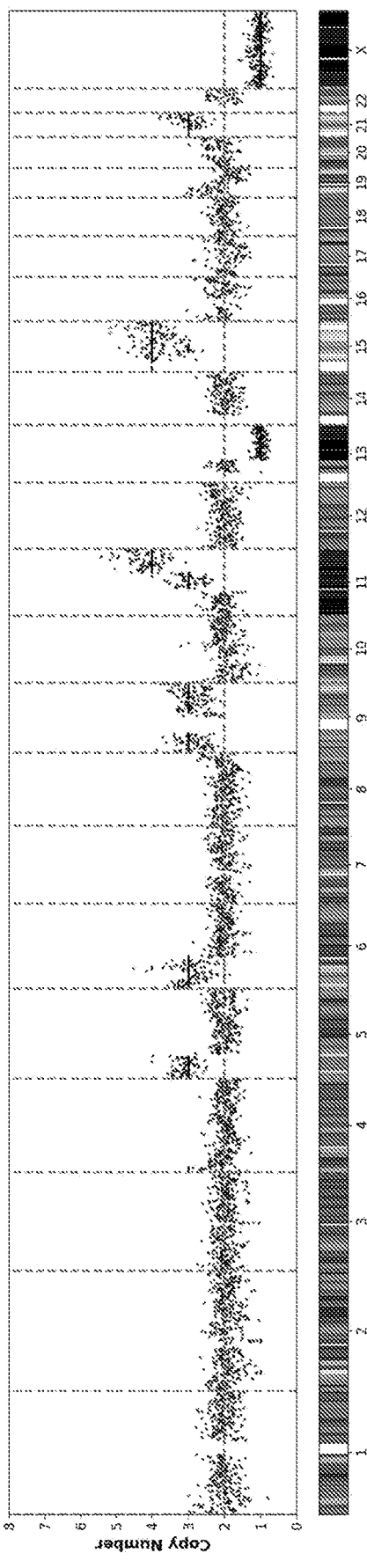
FIG. 16 shows an example of the detection of LoH by using genomic windows with constant number of loci.

FIG. 16 shows the detection of LoH by using genomic windows with constant number of loci. In particular, a copy-number plot of the same CTC of Example 1 is shown on top. On the x axis are the chromosomes; on the y axis is the copy number. Each dot represents a genomic window of fixed size. Copy number segments are represented as solid lines. Below the plot is a heatmap representing the heterozygous count for each genomic window. Windows with a lower LoH score (lower number of Heterozygous loci), which are more likely to be in LoH status, are represented by a deeper shade of gray. Chromosome 11, large arm of chromosome 13 and chromosome X (which is in single copy in a male individual) show the lower LoH score.

Figure 17:
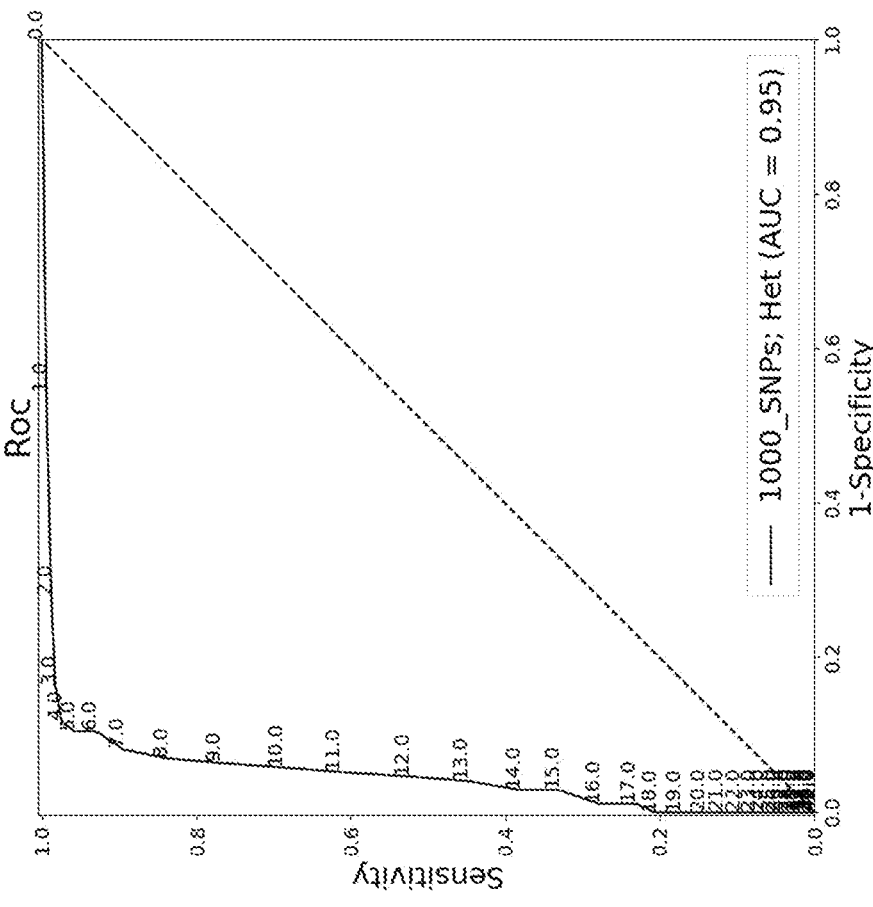
FIG. 17 shows a ROC curve created based on a training set of 9 single cells for the identification of an LoH score threshold, defined as the number of heterozygous loci in a window of n=1000 SNPs covered by at least 1 reads with 1.000.000 mapped reads.

To determine a LoH score threshold to call genomic windows in LoH status, a training set of 9 single cells with known LoH regions was analyzed using the same methodology as the test sample (1.000.000 mapped reads and n=1000 SNPs windows). A ROC analysis was then performed and a maximum LoH score threshold=6 was determined as the point of best tradeoff between sensitivity and specificity (FIG. 17, in which the x axis represents 1-specificity (lower values mean a more specific detection) and the y axis represents sensitivity. LoHs detected in the tumor cell by high pass whole genome sequencing were used as reference).

Figures 18, 19:
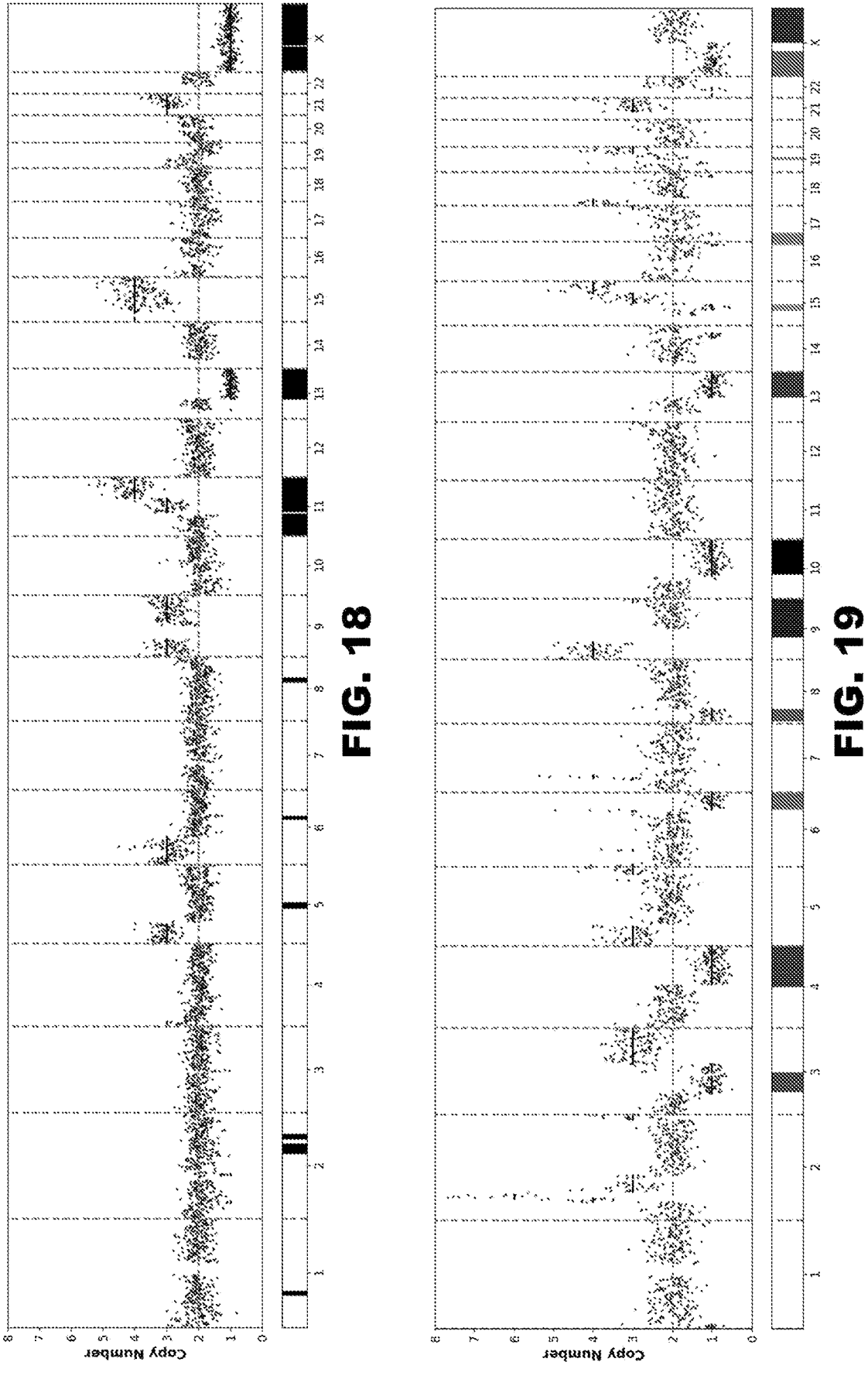
FIG. 18 shows a plot of a single tumoral cell and LoH genomic regions detected according to the method in Example 2 of the invention.
FIG. 19 shows an example of the detection of genomic regions with LoH status using copy number segmentation and Fisher test.

The method identified LoH events on chromosomes 11 and 13 successfully. LoH status is also assigned to chromosome X as expected in a male individual whose genome contains a single copy of X chromosome (FIG. 18—Regions with an LoH score under a fixed threshold (<=6) and larger than 10.000.000 bp are shown in black).

Example 3

In Example 3, Amplil LowPass for Illumina libraries of 2 single Hodgkin Reed/Sternberg (HRS) cells obtained from a FFPE tissue of a classical Hodgkin Lymphoma sample from a male patient were analyzed. The two HRS cells share the same copy number profile. The sequenced reads were mapped to the hg19 reference human genome and the alleles present at dbSNP polymorphic loci (dbSNP150 common variants with a minor allele frequency ≥5%) were extracted from both libraries. Loci were partitioned using copy number segments obtained by using Control-FREEC software, implementing GC-based normalization and copy number signal segmentation [Boeva, V. et al., "Control-free calling of copy number alterations in deep-sequencing data using GC-content normalization," Bioinformatics, 27(2), 268-269 (2011). An internal control defined by the union of all the regions with copy number equal to cell's ploidy (copy number=2) was used. For each segment, defined by copy number analysis and contained in a chromosome arm, a one-sided Fisher Exact test was performed to reject the null hypothesis that the observed biallelic and monoallelic loci are equally likely in the segment and in the internal control (FIG. 19—on top: one representative HRS cell copy number profile. Below: heatmap of $-\log_{10}$ of p-value obtained as output of Fisher test. Only genomic regions with p-values 0.01 are displayed. More significant values are represented by a deeper shades of gray). As expected, all regions with copy number=1 were correctly detected as LoH genomic regions. Despite having copy number=2, the long arm of chromosome X is detected in LoH status. This is expected as the sample is from a male individual and thus the genome contains a single X chromosome. In addition, chromosome 9q is called in LoH, which would be missed by only using the copy-number information (copy-number=2).

Advantages

The method according to the present invention is suitable to analyze data obtained from low-pass sequencing of genomic DNA from a test sample to detect LoH events. Contrary to other methods, inferring LoHs as runs of contiguous homozygous loci and requiring to extract the real genotype at a certain number of loci, the method of the present invention is based on the principle that, by analyzing a genomic window containing a sufficient number of loci sequenced at low coverage, and by extracting the alleles observed at said loci, not necessarily representative of the sample genotype, it may be possible to detect an LoH event as a decrease in biallelic loci, compared to that observed by analyzing a normal diploid sample.

Contrary to other methods, inferring LoH from the alternative-allele frequency (B Allele Frequency or BAF), demanding a high-coverage of the genome, such as for example 30× (Boeva et al., Bioinformatics, Vol. 28 no. 3 (2012), pages 423-42), the method according to the invention works with low-pass whole genome sequencing data (<1x, or lower, down to e.g. 0.05× or even 0.01×), with corresponding cost savings.

The method for analyzing LoH from a sample according to the present invention allows to infer LoH regions across the genome from low-pass whole genome sequencing data down to the single-cell resolution, using very few samples, as it may be the case where only few (down to a single one) CTCs are available, with the additional optional possibility to run the analysis without a normal control, and with a relatively small number of reads.

Further, particular embodiments of the method enable to increase the resolution in LoH calling by introducing certain processing steps in the library preparation process, without incremental sequencing costs.

The method according to the invention surprisingly advances the state of the art with performances previously thought unachievable by the skilled in the art. In particular, the method allows to:

identify LoH on a single-cell by low-pass whole-genome sequencing with as low as 0.01-0.04 mean coverage (250,000-1,000,000 single-end 150 bp reads of the human genome);

obtain the above point without a control sample;

obtain the above points with the further possibility of obtaining additional genetic material for investigation of other characteristics of said single-cell, as well as the possibility to reliably reanalyse a single cell for verification, in virtue of the use of an inherent WGA in the process.

In addition, the method according to the present invention allows to determine whole-genome copy number profile and LoH even from minute amount of cells, FFPE or tissue biopsies.

The invention claimed is:

1. A method for analyzing loss-of-heterozygosity (LoH) in at least one sample comprising genomic DNA, the method comprising the steps of:

a. providing the at least one sample comprising genomic DNA;

b. carrying out a deterministic restriction-site whole genome amplification (DRS-WGA) of said genomic DNA;

c. preparing a massively parallel sequencing library from the product of said DRS-WGA;

d. carrying out low-pass whole genome sequencing at a mean coverage depth of <1 on said massively parallel sequencing library;

e. aligning the reads obtained in step d. on a reference genome for said at least one sample;

f. extracting the allelic content at a plurality of loci, wherein said plurality of loci comprises polymorphic loci and/or heterozygous loci;

g. assigning at least one LOH score, each LoH score, corresponding to a genomic window of said reference genome, for said at least one sample as a function of the number of loci with at least two different alleles in said plurality of loci.

2. The method according to claim 1, further comprising performing a step of fragment size selection before, during or after said step c. of preparing a massively parallel sequencing library and said step of preparing a massively parallel sequencing library does not include a random fragmentation step.

3. The method according to claim 2, wherein said step of size-selection retains fragments in the range from 100 to 800 base pairs.

4. The method according to claim 3, wherein said step of size selection retains fragments in the range from 300 to 450 base pairs.

5. The method according to claim 3, wherein the peak of fragments retained in said step of size-selection is centered on a base pair range from 150 bp to 600 bp.

6. The method according to claim 5, wherein said step of size selection step retains fragments in the range 425-575 base pairs.

7. The method according to claim 1, wherein said at least one genomic window has a constant width in base pairs.

8. The method according to claim 7, wherein each LoH score corresponds to the number of heterozygous loci in said genomic window.

9. The method according to claim 8, wherein, if said LoH score passes a threshold for a genomic window, said genomic window is called as being in LoH.

10. The method according to claim 9, further comprising a step of assigning an LoH status to at least one genomic region if each LoH score for each genomic window comprised in that region passes said threshold.

11. The method according to claim 10, wherein said at least one genomic region comprises a tumor suppressor gene.

12. The method according to claim 11, wherein said tumor suppressor gene is selected from the group consisting of:
   a. BRCA1
   b. BRCA2
   c. PALB2
   d. TP53
   e. CDKN2A
   f. RB1
   g. APC
   h. PTEN
   i. CDKN1B
   j. DMP1
   k. NF1
   l. AML1
   m. EGR1 n. TGFBR1
   o. TGFBR2
   p. SMAD4.

13. The method according to claim 9, further comprising a step of assigning an LoH status to at least one genomic region as a function of the LoH status of genomic windows comprised in that region.

14. The method according to claim 1, wherein said at least one genomic window has a constant number of said plurality of loci.

15. The method according to claim 1, wherein said at least one genomic window is selected from the group consisting of a chromosome, a chromosome arm, and a segmented copy-number region.

16. The method according to claim 1, wherein said plurality of loci comprises polymorphic loci for the reference genome for said at least one sample.

17. The method according to claim 16, wherein each LoH score corresponds to the proportion of heterozygous loci with respect to the total number of said polymorphic loci in the at least one genomic window.

18. The method according to claim 16, wherein each LoH score corresponds to the p-value of a statistical test.

19. The method according to claim 18, wherein said statistical test assesses the significance of over-representation of biallelic loci with respect to sequencing and WGA error rates.

20. The method according to claim 18, wherein said statistical test assesses the significance of under-representation of biallelic loci with respect to a control sample.

21. The method according to claim 20, wherein said control sample comprises at least one genomic region at main ploidy from said at least one sample.

22. The method according to claim 20, wherein said control sample is an at least one normal sample.

23. The method according to claim 22, wherein said at least one normal sample is obtained from the same individual under test from which said at least one sample was obtained.

24. The method according to claim 20, wherein said control sample is a maternal or paternal sample, for said at least one sample.

25. The method according to claim 1, wherein said at least one sample has a purity of at least 50%.

26. The method according to claim 25, wherein said at least one sample is a single cell.

27. The method according to claim 1, wherein in step d low-pass whole genome sequencing is carried out at a mean coverage depth of <0.05 on said massively parallel sequencing library.

28. The method according to claim 1, wherein in step d low-pass whole genome sequencing is carried out at a mean coverage depth of <0.01 on said massively parallel sequencing library.

* * * * *